(12) United States Patent
Sirkar et al.

(10) Patent No.: US 9,993,436 B2
(45) Date of Patent: Jun. 12, 2018

(54) POROUS HOLLOW FIBER ANTI-SOLVENT CRYSTALLIZATION-BASED CONTINUOUS METHOD OF POLYMER COATING ON SUBMICRON AND NANOPARTICLES

(71) Applicant: New Jersey Institute of Technology, Newark, NJ (US)

(72) Inventors: Kamalesh Sirkar, Bridgewater, NJ (US); Robert Pfeffer, Scottsdale, AZ (US); Dengyue Chen, Harrison, NJ (US); Dhananjay Singh, Kearny, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 199 days.

(21) Appl. No.: 14/968,456

(22) Filed: Dec. 14, 2015

(65) Prior Publication Data
US 2016/0166512 A1 Jun. 16, 2016

Related U.S. Application Data

(60) Provisional application No. 62/091,303, filed on Dec. 12, 2014.

(51) Int. Cl.
*A61K 9/50* (2006.01)
*A61K 31/343* (2006.01)
*A61K 9/00* (2006.01)

(52) U.S. Cl.
CPC .......... *A61K 9/5089* (2013.01); *A61K 9/0092* (2013.01); *A61K 31/343* (2013.01); *A61K 9/5026* (2013.01); *A61K 9/5031* (2013.01)

(58) Field of Classification Search
CPC ....................................................... A61K 9/14
(Continued)

(56) References Cited

U.S. PATENT DOCUMENTS

| 5,314,506 | A | 5/1994 | Midler et al. |
| 2007/0289105 | A1* | 12/2007 | Sirkar ................ B01D 63/02 |
|  |  |  | 23/295 R |
| 2015/0125590 | A1* | 5/2015 | Sirkar ................ A61K 9/5192 |
|  |  |  | 427/2.14 |

OTHER PUBLICATIONS

Guiot, P. et al., Polymeric Nanoparticles and Microspheres : Chapter 1 Nanoparticulate Drugy Delivery Systems Based on Gelatin and Albumin, Boca Raton, CRC Press, pp. 1-25, 1986.
(Continued)

*Primary Examiner* — Dah-Wei D Yuan
*Assistant Examiner* — Andrew Bowman
(74) *Attorney, Agent, or Firm* — McCarter & English, LLP

(57) ABSTRACT

Using porous hollow fiber membranes, systems/methods for continuously synthesizing polymer-coated particles by anti-solvent crystallization are provided. The disclosed systems/methods provide for synthesis of polymer-coated drug particles/crystals from solutions of the polymer and the drug particles in suspension by exposing the solution to an anti-solvent through a porous hollow fiber device. A feed solution of a coating polymer with suspended drug particles can be exposed to an anti-solvent through hollow fiber pores, thereby causing the polymer to precipitate on and coat the drug particles. In addition, a feed solution of a coating polymer with drug in solution can be exposed to an anti-solvent through hollow fiber pores, thereby causing the drug to crystallize from the solution and the polymer to precipitate/coat the drug. Results indicate that a uniformly coated, free-flowing product may be developed in this advantageous porous hollow fiber anti-solvent crystallization method. The coated drug particles can be used for controlled release of the drug, and the molecule and the crystal structure are not affected by the process.

19 Claims, 17 Drawing Sheets

(58) Field of Classification Search
USPC .......................................................... 427/2.14
See application file for complete search history.

(56) References Cited

OTHER PUBLICATIONS

Tavare, N.S; Micromixing Limits in an MSMPR Crystallizer, Chemical Engineering Technology 1989, 12, 1-12.

Langer, R. New Methods of Drug Delviery. Science, 249 (4976), 1527-1533, 1990.

Tsutsumi, A. et al., A Novel Fuidized-bed Coating of Fine Particles by Rapid Expansion of Supercritical Fluid Solutions. Powder Technol. 85, 275-278, 1995.

Kim, J.H. et al., Microencapsulation of Naproxen using Rapid Expansion of Supercritical Solutions, Biotechnol. Prog. 1996, 12, 650-661.

Falk, R. et al., Controlled Release of Ionic Compounds from Poly (L-lactide) Microspheres Produced by Precipitation with a Compressed Antisolvent, Journal of Controlled Release, 44 (1997) 77-85.

Leong, K.W. et al., DNA-polycation Nanospheres as Non-viral Gene Delivery Vehicles, Journal of Controlled Release, 53 (1998) 183-193.

Pessey, V. et al., $SmCo_5$/Cu Particles Elaboration using a Supercritical Fluid Process, Journal of Alloys and Compounds, 323-324 (2001) 412-416.

Myerson, A.S. Handbook of Industrial Crystallization, 2nd Ed. Butterworth-Heinemann, Boston, MA (2002).

Wang, Y. et al., Polymer Coating/encapsulation of Nanoparticles using a Supercritical Anti-solvent Process, J. of Supercritical Fluids, 28 (2004) 85-99.

Yue, B. et al., Particle Encapsulation with Polymers via in situ Polymerization in Supercritical $CO_2$, Powder Technology, 146 (2004), 32-45.

Gelperina, S. et al., The Potential Advantages of Nanoparticle Drug Delivery Systems in Chemotherapy of Tuberculosis, American Journal of Respiratory and Critical Care Medicine, 172 (2005) 1487-1490.

Oh, K. S. et al., Formation of Core/Shell Nanoparticles with a Lipid Core and Their Application as a Drug Delivery System. Biomacromolecules, 2005, 6 (2), 1062-1067.

Stejskal, J. et al., Coating of zinc ferrite particles with a conducting polymer, polyaniline, Journal of Colloid and Interface Science, 298 (2006) 87-93.

Zarkadas, D.M. et al., Antisolvent Crystallization in Porous Hollow Fiber Devices, Chemical Engineering Science, 61 (2006) 5030-5048.

Lai, S.K. et al., Mucus-penetrating nanoparticles for drug and gene delivery to mucosal tissues, Advanced Drug Delivery Review, 61 (2009), 158-171.

Chen, D. et al., Continuous Polymer Coating/Encapsulation of Submicrometer Particles using a Solid Hollow Fiber Cooling Crystallization Method, Ind. Eng. Chem. Res., 2014, 53, 6388-6400.

Chen, D. et al., Continuous Polymer Nanocoating on Silica Nanoparticles, Langmuir, 2014, 30, 7804-7810.

Korin, N. et al., Shear-Activated Nanotherapeutics for Drug Targeting to Obstructed Blood Vessels, Science, 2012, 337, 738-742.

Nance, Elizabeth A. et al., A Dense Poly(ethylene glycol) Coating Improves Penetration of Large Polymeric Nanoparticles within Brain Tissue, Science Translational Medicine 2012, 4 (149), 1-18.

U.S. Appl. No. 62/091,303, filed Dec. 12, 2014.

\* cited by examiner

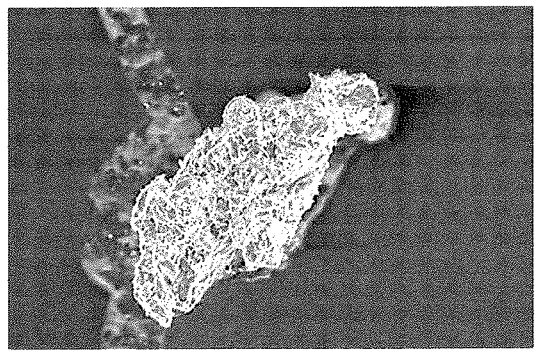
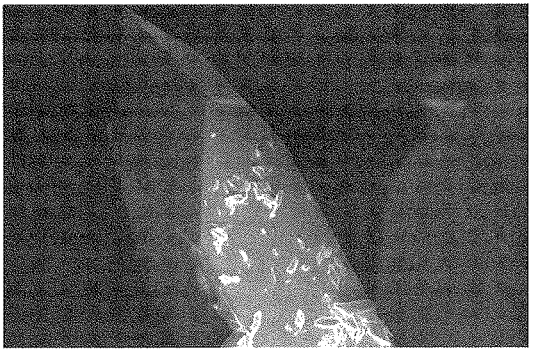
FIGURE 3A          FIGURE 3B
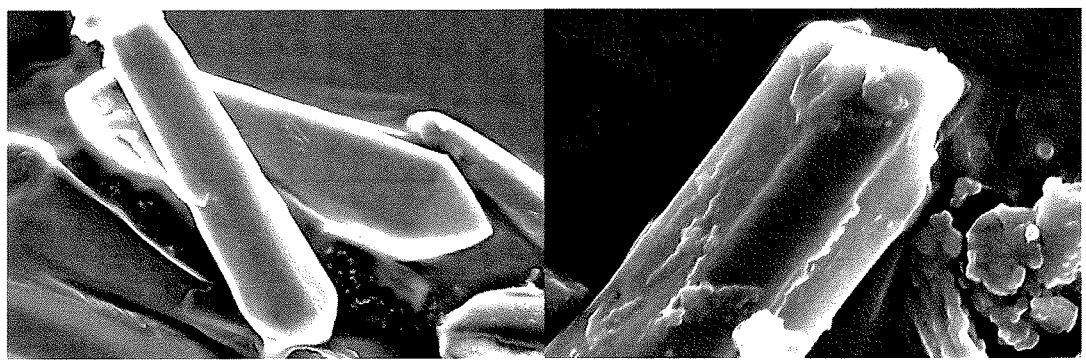
FIGURE 3C          FIGURE 3D

FIGURE 3E  FIGURE 3F

POROUS HOLLOW FIBER ANTI-SOLVENT CRYSTALLIZATION-BASED CONTINUOUS METHOD OF POLYMER COATING ON SUBMICRON AND NANOPARTICLES

CROSS-REFERENCE TO RELATED APPLICATIONS

This application claims the benefit of U.S. Provisional Application entitled "Porous Hollow Fiber Anti-Solvent Crystallization-Based Continuous Method of Polymer Coating on Submicron and Nanoparticles," which was filed on Dec. 12, 2014, and assigned Ser. No. 62/091,303, the contents of which are herein incorporated by reference in their entirety.

STATEMENT REGARDING FEDERALLY SPONSORED RESEARCH

This invention was made with government support under Grant CMMI-1100622 awarded by the National Science Foundation. The government has certain rights in this invention.

FIELD OF THE DISCLOSURE

The present disclosure is directed to advantageous systems and methods for anti-solvent crystallization based synthesis of coated drug particles from solutions containing the drug and the coating polymer. The present disclosure is also directed to advantageous systems and methods in which drug crystals that are in suspension are coated with polymers from solutions (e.g., acetone solutions) based on exposure to an anti-solvent introduced through a porous membrane/hollow fiber device.

The present disclosure provides advantageous systems and methods utilizing the disclosed porous membrane-based anti-solvent crystallization technique, including systems and methods wherein a feed solution of a coating polymer with suspended drug particles or drug in solution is exposed to an anti-solvent through membrane/hollow fiber pores, thereby causing the polymer to precipitate and coat the drug particles, thereby yielding a continuous process for coating drug particles using the disclosed anti-solvent crystallization technique. In instances where the drug is in solution, the drug first precipitates from the solution as crystals or particles, and generally functions as nuclei for the precipitating coating polymer. In instances where the drug particles are suspended in the solution, introduction of the anti-solvent causes the polymer to precipitate from the solution and to coat the drug particles.

BACKGROUND OF THE DISCLOSURE

In controlled drug delivery systems, well-characterized and reproducible dosage forms are utilized to ensure that the rate and duration of drug delivery achieves the required concentration in the host. Usually there is a concentration range for each drug which provides optimal therapeutic effects: higher concentration may cause toxicity whereas a lower one may be therapeutically ineffective. Controlled delivery is usually achieved by a number of methods; two common ones employ either a matrix system where the drug is dispersed in a polymer matrix or a microencapsulation system where the individual drug particle is encapsulated in a polymeric coating. The polymeric coating can also provide protection for fragile drugs from hydrolysis and degradation for example by providing protection from stomach acids.

The size range of drug particles can vary between micron-sized, sub-micron and nanoparticles. Due to their greater solubility, high stability, high carrier capacity, incorporation of biodegradable and hydrophobic/hydrophilic substances and administration by a variety of delivery vehicles, nanoparticle-based systems have attracted considerable attention in controlled release of drugs, delivery of anticancer drugs and imaging agents to tumors, tuberculosis treatment and as non-viral gene delivery vehicles. When coated with lower molecular weight polyethylene glycol, nanoparticles could traverse the physiological human mucous rapidly. Dense polyethylene glycol coating improved penetration of polymeric nanoparticles within brain tissue in cases where the blood-brain barrier is compromised. Polymer-coated nanoparticles are also being utilized in chemical, electronic, optical and physical applications.

A variety of methods have been conventionally employed to coat micron-sized, submicron and nanoparticles with a polymer. Physical vapor deposition, plasma treatment, chemical vapor deposition, and pyrolysis of polymeric organic materials are examples of dry methods, and sol-gel processes, emulsification and solvent evaporation techniques are examples of wet methods. Additional methods for polymer coating or encapsulation of nanoparticles and ultrafine particles employing supercritical $CO_2$ include: Rapid Expansion of Supercritical Solutions (RESS), Supercritical Anti-Solvent (SAS), and Gas Anti-Solvent (GAS) processes. These processes have many shortcomings, such as very high pressures, and low solubility of polymers (many of which may also lack biodegradability). Furthermore, these are batch processes and it is problematic to develop the needed drug production capacities.

Although fluidized bed-based coating processes can be continuous, there are problems due to scale-up difficulties as well as agglomeration of smaller (submicron and nano) particles resulting from van der Waals and other interparticle forces; the polymer coating will enhance the agglomeration tendencies. Conventional batch crystallization devices, if used for coating, will suffer from imperfect mixing and non-uniform conditions leading to extreme variability of the product.

Conventional crystallization/precipitation typically relies on processes employing cooling, solvent evaporation, anti-solvent addition and precipitation by reaction. For anti-solvent addition-based processes, a technique of increasing interest in pharmaceutical processing is the use of an impinging-jet mixer, where two high velocity streams are brought into contact to effect high nucleation rates, followed by growth in a well-mixed vessel or a tubular precipitator. There are a number of well-known shortcomings of this technique. As referenced above, the SAS, GAS and related supercritical anti-solvent techniques are batch processes which require very demanding experimental conditions.

Despite efforts to date, a need remains for efficient and effective systems and methods to continuously coat submicron and nano-sized particles. In particular, a need remains for systems and methods for effective coating of submicron and nano-sized drug particles. These and other needs are addressed according to the present disclosure.

SUMMARY OF THE DISCLOSURE

The present disclosure provides advantageous systems and methods for continuous polymer coating of particles (e.g., nanoparticles). In exemplary embodiments, the present disclosure provides for the synthesis of polymer-coated drug crystals from solutions of the polymer and the drug by exposing the solution to an anti-solvent through a porous membrane/hollow fiber device.

The disclosed systems and methods may advantageously utilize the disclosed porous membrane-based anti-solvent crystallization technique, wherein a feed solution of a coating polymer with suspended drug particles or drug in solution is exposed to an anti-solvent through membrane/hollow fiber pores, thereby causing the polymer to precipitate and coat the drug particles, thereby yielding a continuous process for coating drug particles using the disclosed anti-solvent crystallization technique. In instances where the drug is in solution, the drug first precipitates from the solution as crystals or particles, and generally functions as nuclei for the precipitating coating polymer. In instances where the drug particles are suspended in the solution, introduction of the anti-solvent causes the polymer to precipitate from the solution and to coat the drug particles. In certain embodiments, the present disclosure embraces continuous coating of particles from about 1 nm to about 10 microns.

The present disclosure provides for a method for coating particles, e.g., drug particles, that may operate in systems where the drug is in a polymer solution, and systems wherein the drug is in the form of drug particles that are suspended in the polymer solution. Thus, in exemplary implementations, the present disclosure provides a method/system for coating particles, e.g., drug particles, that involves:

a) providing a solution containing a polymer and a drug;
b) passing the solution through a lumen of a hollow fiber or around an exterior to the hollow fiber; and
c) passing an anti-solvent around the exterior of the hollow fiber in an instance where the solution is passed through the lumen of the hollow fiber, or through the lumen of the hollow fiber in an instance where the solution is passed around the exterior to the hollow fiber, so that the anti-solvent or the solution permeates through pores of the hollow fiber and travels to the lumen of the hollow fiber and exposes the anti-solvent to the solution, thereby causing the polymer to precipitate on the drug, with precipitated polymer forming a coating on the particles of the drug. In exemplary implementations, the drug is suspended in the polymer solution. In other exemplary embodiments, the drug is in solution in the polymer solution, and the drug precipitates from the polymer solution in response to exposure to the anti-solvent.

Any combination or permutation of embodiments is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the scope of the present disclosure. To assist those of ordinary skill in the art in making and using the disclosed systems, assemblies and methods, reference is made to the appended figures, wherein:

FIGS. 3A-3F. SEM micrographs related to experimental results associated with exemplary implementation of the present disclosure: FIG. 3A is an SEM micrograph of pure Griseofulvin (GF) drug powder as received; FIG. 3B is an SEM micrograph of pure GF drug particles after precipitation in a PHFAC device without any polymer; FIGS. 3C and 3D are SEM micrographs of polymer coated GF drug crystals after precipitation; FIG. 3E is an SEM micrograph of uncoated GF sample prepared under flow-rate combination X0 (see Table 1); and FIG. 3F is an SEM micrograph of polymer-coated GF crystals prepared using flow-rate combination X1 (Table 1).

FIG. 10A is SEM micrograph of uncoated silica (Cosmo 55) and FIG. 10B is SEM micrograph of Eudragit-coated silica (Cosmo 55) under different magnifications.

FIG. 14A is 10 wt % PLGA and FIG. 14B is 2.5 wt % PLGA.

DETAILED DESCRIPTION OF DISCLOSURE

According to the present disclosure, a continuous system and method are provided whereby drug particles (e.g., micron-size drug particles) having a thin polymeric coating are continuously and effectively produced. In exemplary embodiments of the present disclosure, the disclosed system and method have been utilized to continuously produce micron-sized drug particles having a thin polymeric coating from a solution (e.g., an acetone solution) of the drug as well as the polymer used to coat it. In other exemplary embodiments of the present disclosure, the disclosed system and method have been utilized to continuously produce micron-sized drug particles having a thin polymeric coating from a feed system where the drug particles are in suspension.

For example, submicron (e.g., 550 nm) and nanoparticles (e.g., 12 nm silica) may be coated continuously with thin layers of polymers (e.g., Eudragit RL 100 and PLGA) according to the present disclosure. In exemplary implementations, the present disclosure provides a facile and continuous method of synthesizing micron-size drug particles (e.g., Griseofulvin drug particles) having a polymer coating using a porous hollow fiber membrane-based anti-solvent crystallization method (e.g., with Eudragit RL 100 polymer coatings on the crystallized drug particles). To form the disclosed polymer-coated drug particles, the polymer coating may form with respect to drug that is initially in solution or drug particles that are in suspension. In some embodiments, the present disclosure embraces continuous coating of particles from about 1 nm to about 10 microns.

Although the present disclosure is described with reference to exemplary embodiments and implementations, it is to be understood that the present disclosure is not limited by or to such exemplary embodiments/implementations.

a. Porous Hollow Fiber Anti-Solvent Crystallizer/Precipitator

Figure 1A:
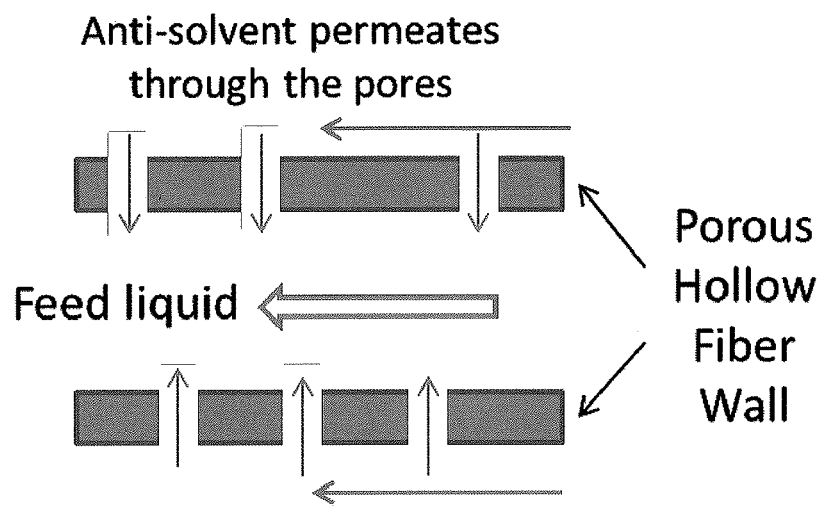
FIGS. 1A-1D. Porous hollow fiber anti-solvent crystallization (PHFAC) operating approach for permeation of anti-solvent or feed liquid through the pores according to the present disclosure. For implementations wherein the anti-solvent permeates through the pores, FIG. 1A schematically depicts crystallization in the tube side whereas FIG. 1B schematically depicts crystallization in the shell side. For implementations wherein the feed liquid permeates through the pores, FIG. 1C schematically depicts crystallization in the tube side whereas FIG. 1D schematically depicts crystallization in the shell side.
Figure 1B:
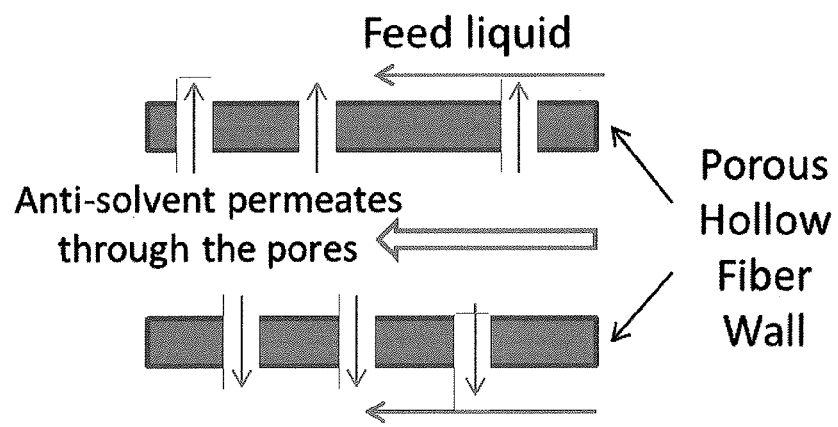

Two potential configurations of a single porous hollow fiber anti-solvent crystallizer (PHFAC) are shown in FIGS. 1A and 1B. The porous hydrophilic hollow fiber may be made of the polymer Nylon 6 which has excellent resistance to pH and a variety of organic solvents. This fiber may have an inner diameter (ID) on the order of about 600 µm and an outer diameter (OD) on the order of about 1000 µm. The hollow fiber wall porosity may be on the order of about 0.75; exemplary pore size ranges from about 0.2 to about 1.5 µm with only a few pores having the largest size. As will be readily apparent to persons skilled in the art, other types of porous hollow fibers may also be used according to the present disclosure.

Anti-solvent crystallization using the hollow fiber-based membrane may be carried out in at least two ways shown in FIGS. 1A and 1B. In both of these configurations, the anti-solvent is adapted to permeate through the pores of the porous hollow fiber. Configurations wherein the polymer feed suspension is made to permeate through the pores generally are not possible for this particular hollow fiber selected because, in the case of submicron particles, the diameter of the host silica particles used (0.55 µm) is larger than most of the pores. Some agglomeration of the silica particles can occur in the feed suspension leading to clogging of the pore mouths.

FIG. 1A illustrates an exemplary implementation of the present disclosure wherein polymer crystallization/precipitation takes place in the tube/lumen side. The feed polymer solution containing the dissolved drug species flows through the fiber lumen side while the anti-solvent permeates from the shell side (e.g., from the exterior of the hollow fiber) through the pores of the hollow fiber and into the lumen. In exemplary embodiments, the shell side pressure is kept at a higher level than the lumen side to maintain a certain permeation rate for the anti-solvent. The polymer as well as the drug crystallizes from the solution due to the introduction of the anti-solvent through the membrane pores. The drug crystals may be formed rapidly and are thereafter coated by the precipitating/crystallizing polymer molecules in the tube side solution. Thus, the anti-solvent permeates through the pores from the shell side into the tube/lumen side, while the feed polymer solution-suspension of particles flows in the tube/lumen side. Injection of the anti-solvent through numerous pores generates intense mixing between the two liquids leading to precipitation of the polymer and covering of the host particles present in the feed solution-suspension in the tube/lumen side.

FIG. 1B illustrates a reversed configuration. The feed solution-suspension is pumped through the shell side; the anti-solvent is pumped through the tube/lumen side such that the anti-solvent permeates into the shell side as numerous jets streaming into the polymer solution-suspension. The anti-solvent flowing in the tube/lumen side at a higher pressure flows into the shell side where the acetone solution containing the dissolved drug molecules and the polymer is flowing. In this case, the tube/lumen side pressure should be maintained at a higher level than the shell side so that the anti-solvent can flow through the pores into the shell side. Crystallization takes place in the shell side with both the drug and the polymer precipitating; the rapidly crystallizing drug particles get immediately coated by the precipitating polymer, e.g., rapid precipitation/crystallization of drug particles in the shell side and polymer coating of the drug particles. In certain embodiments and due to the larger cross-sectional area in the shell side, particles are more easily swept away compared to that in the tube side crystallization and precipitation technique, because the internal diameter of the single hollow fiber is less than the average inter-fiber spacing on the shell side as well as the inter-fiber gap dimensions can be much larger than the tube side diameter if the shell side void volume fraction is large. Exemplary experimental results described herein were generated using the configuration shown in FIG. 1B.

Figure 1C:
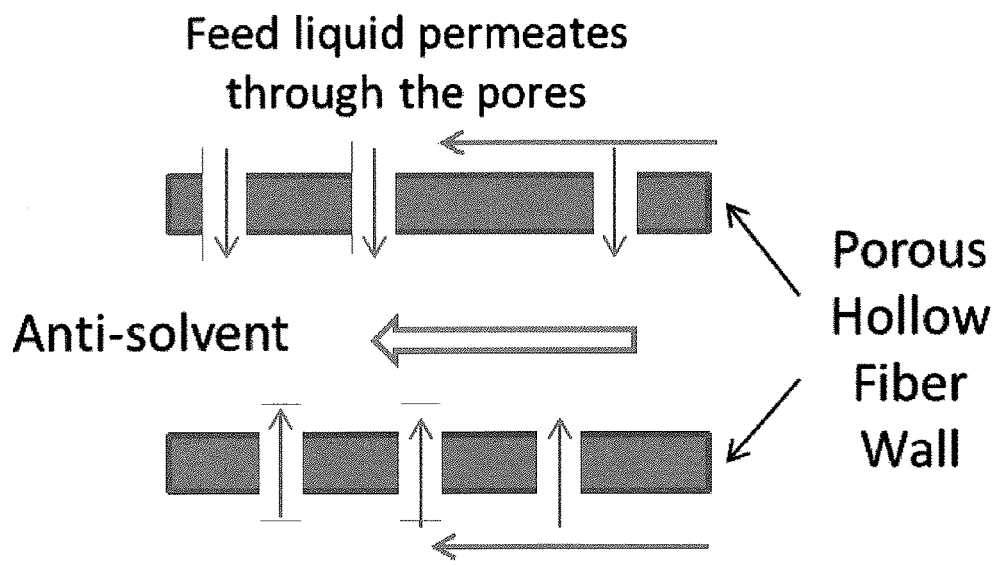
Figure 1D:
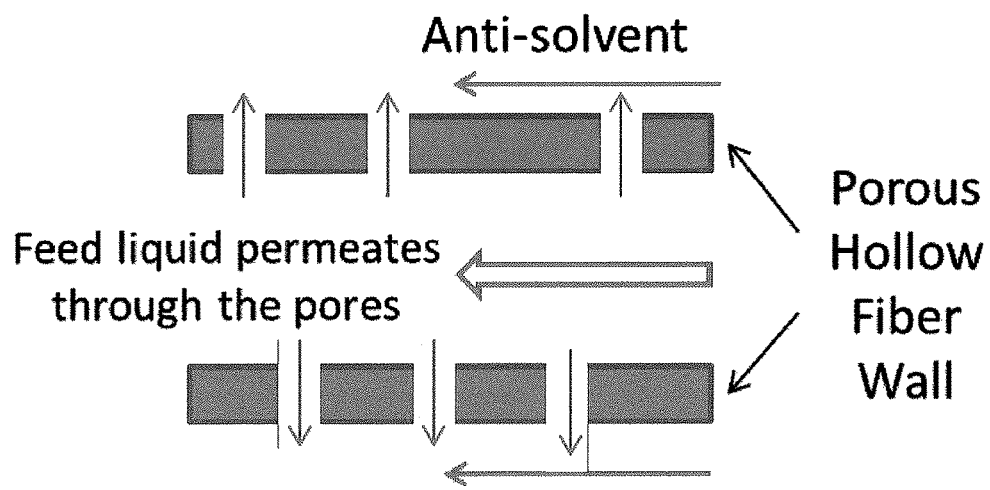

Two other potential operational configurations of the porous hollow fiber-based anti-solvent crystallizer (PHFAC) technique are shown in FIGS. 1C and 1D. The alternative configurations generally involve passing the feed solution through the membrane pores. However, in these configurations, there may be an undesirable possibility of precipitation occurring in the pores and, for this reason, these configurations may be disadvantageous.

Figure 2A:
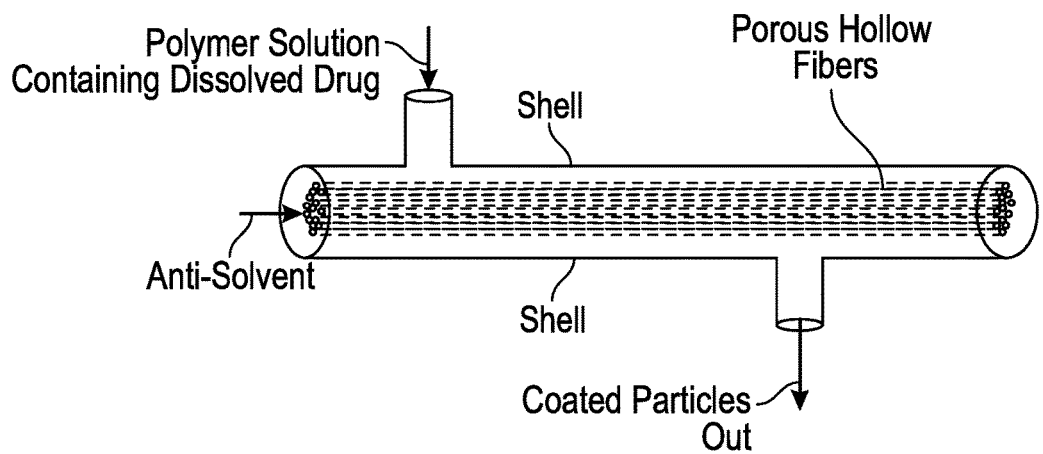
FIG. 2A provides a schematic depiction of an exemplary porous hollow fiber anti-solvent crystallizer (PHFAC) according to the present disclosure.

With reference to FIG. 2A, an exemplary PHFAC module containing a number of porous hollow fibers for continuous synthesis of polymer-coated drug crystals is schematically depicted. As shown in FIG. 1B, each hollow fiber serves as a separate anti-solvent crystallizer. The anti-solvent flowing through the hollow fiber tube/lumen side at a higher pressure permeates to the shell side where the polymer solution containing the dissolved drug molecules is flowing. The mixing efficiency of this process is extraordinary. The rapid local addition of the anti-solvent through substantially every pore mouth drastically decreases the solubility of the drug as well as the polymer in the feed solution; a very high supersaturation is created throughout the shell-side cross section at substantially every axial location in the module causing precipitation of the drug and the polymer resulting in the production of polymer coated drug particles. The suspension of the coated particles along with the excess solution and the anti-solvent continue to be pumped out from an outlet of the shell. In preferred/exemplary embodiments, the drug crystallizes first and functions as nuclei for the precipitating polymer.

This exemplary PHFAC system and process of synthesizing polymer coated drug crystals has advantages compared to the other anti-solvent crystallizers. There is an extraordinarily intense contacting of the anti-solvent and the feed solution substantially everywhere in the shell side of the PHFAC module. Since the fractional porosity of the hollow fiber wall is around 0.75 in exemplary implementations, a large number of hollow fibers will result in anti-solvent jets emanating from innumerable pores substantially everywhere in the membrane module. Therefore, almost the entire shell side will be subjected to an intense contacting due to the very large interfacial area created between the two miscible liquid streams. A very high level of supersaturation is created throughout the shell side resulting in very rapid crystallization of the drug molecules as well as the polymer. The growth of the crystals and the coating thickness will depend on a balance between the rate at which the supersaturation is created locally, the level of supersaturation created and the time allowed for the growth process to occur which is largely determined by the residence time of the shell-side liquid stream.

Another advantage of the disclosed PHFAC device/process is the high surface area/volume ratio that can be achieved if reasonably high packing density of the hollow fiber membranes is provided. The disclosed approach will advantageously lead to maximization of the rate of production of the coated drug particles and achievement of a high product recovery rate. Furthermore, scale up can be expected to be relatively straightforward because the number of hollow fibers in a module can be increased or decreased according to the needs of production; correspondingly, the module shell diameter can be increased or decreased. Theoretically, the larger the number of hollow fibers in the tube side of PHFAC module, the higher the rate of production. The morphology and dimensions of the coated drug particles are likely to remain the same if the flow rates can be increased in proportion to the increase in the number of hollow fibers.

Figure 2B:
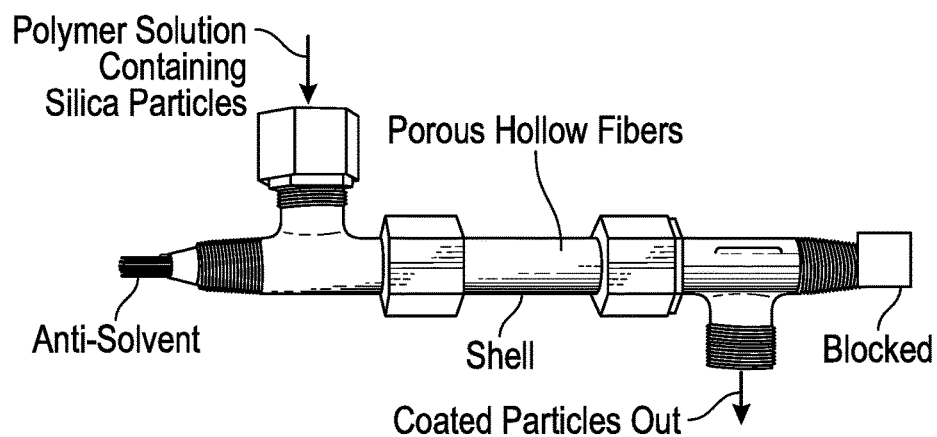
FIG. 2B is a photograph of an exemplary porous hollow fiber-based anti-solvent crystallizer (PHFAC) according to the present disclosure.

With reference to FIG. 2B, a photograph of an exemplary porous hollow fiber-based anti-solvent crystallizer (PHFAC) according to the present disclosure is provided. The exemplary/depicted PHFAC contains 23 porous nylon hollow fibers inside the shell which is made of fluorinated ethylene propylene (FEP). The shell internal diameter is 8 mm and the effective length is 8 cm. The two ends of the hollow fibers at the end of the shell side tube were potted with polypropylene male run tees (Cole-Parmer, Vernon Hills, Ill.) using an epoxy resin (C4 and D, Armstrong, Easton, Mass.). As shown in FIG. 2B, anti-solvent (e.g., water) is passed through the lumen of the hollow fibers in the tube side while the polymer solution containing a suspension of particles may be pumped in the shell side of the module co-currently.

b. Experimental Testing/Results—Experiment #1 i. Materials

Eudragit RL 100 ($M_w$, 150,000; a copolymer of methyl methacrylate, ethyl acrylate and methacrylic acid ester) from Evonik-Degussa (Parsippany, N.J.) was employed as the coating polymer. Drug particles of Griseofulvin (GF) from Letco (Decatur, Ala.) were used without further treatment. The GF drug particles appear to have a solubility of 0.116 M in acetone and are practically insoluble in water. Sodium dodecyl sulfate (SDS) was used as a surfactant (Sigma-Aldrich). Deionized water was used as the tube side anti-solvent liquid. The Nylon 6 hollow fibers were obtained from ENKA America Inc. (Asheville, N.C.).

ii. Preparation of the Feed Solution

As noted above, Eudragit RL 100 polymer was selected as the coating polymer for GF. An amount of 2.4 g of polymer granules was first put in a glass flask containing 20 mL acetone. After about 1 hr when the polymer was fully dissolved, a small amount (4 mL) of the anti-solvent, water, was added to keep the polymer solution highly sensitive to further anti-solvent addition. Next, 0.025 g of SDS was added before the addition of GF to keep the particles to be produced dispersed. Finally, 0.55 g GF powder was added to the acetone solution and, after about 30 min, the solution turned from cloudy to clear, indicating that the GF powder was fully dissolved in the solution.

iii. PHFAC Module Fabrication

Porous Nylon 6 hollow fibers (porosity, 0.75) of 600/1000 μm ID/OD were used to fabricate the PHFAC module. A total of 23 hollow fibers each having an effective length of about 8 cm were placed inside a fluorinated ethylene propylene (FEP) tubing of internal diameter of about 8 mm. The two ends of the FEP tubing were connected to two polypropylene male run tees (Cole-Parmer, Vernon Hills, Ill.). Since the anti-solvent solution which is pumped into the tube side of the hollow fibers permeated to the shell side through the pores in the hollow fiber wall, the other outlet of the tube side was kept closed. The potting of the tube sheet at each end was made in a male run tee using an epoxy resin (mixture of C4 and activator D: Armstrong, Easton, Mass.). After the module was left for 24 hours for curing of the epoxy, water was circulated from the tube side to the shell side to check for any leakage in the module.

iv. Experimental Methods

Figure 2C:
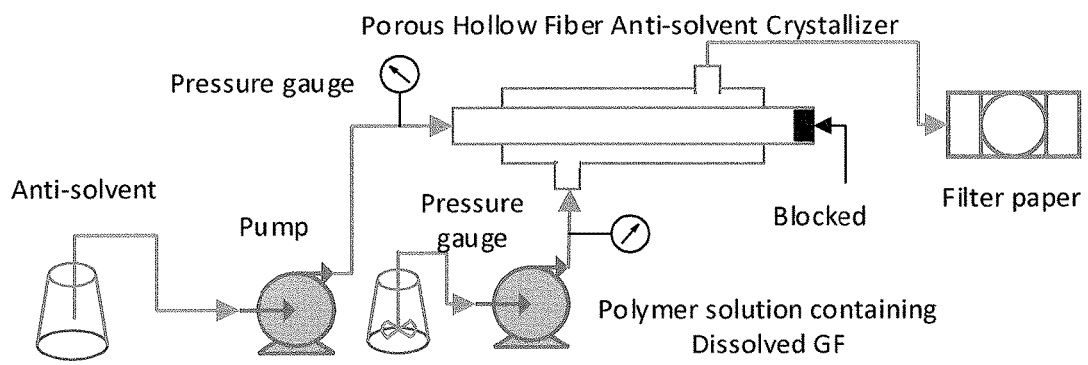
FIG. 2C provides a schematic depiction of an experimental setup for an exemplary porous hollow fiber anti-solvent crystallization/coating system for continuous coating of drug in solution according to the present disclosure.

A schematic diagram of porous hollow fiber anti-solvent crystallization/coating setup for developing polymer coated GF drug particles according to the present disclosure is shown in FIG. 2C. A flask containing the solution of dissolved GF and polymer was placed over a magnetic stirrer. A peristaltic pump (Masterflex L/S model 7518-60, Cole-Parmer, Vernon Hills, Ill.) was used to first pump DI water to the tube side. Subsequently, the polymer-drug solution was passed into the shell side of the PHFAC module by another peristaltic pump after 2 min. Since the other end of the tube side was blocked, water was forced to go through the pores in the hollow fiber membrane into the shell side. Innumerable tiny water jets from the pores were injected into the acetone solution of the drug and the polymer on the shell side, generating intense mixing of the feed solution with water. The anti-solvent water dramatically increases the supersaturation by decreasing the solubility of the drug as well as the polymer in the resulting solution. The tube side water flow rate was kept at about 11 mL/min while the shell side flow rate for the drug-polymer solution was maintained at about 6 mL/min (unless otherwise mentioned; other flow rate combinations were also used and will be identified below). The pressure difference maintained between the shell side and tube side was 15 psi.

Crystals of Griseofulvin appeared and the polymer precipitated from the solution rapidly encapsulating the Griseofulvin drug crystals. Indeed, heterogeneous nucleation of the polymer occurred around the growing drug crystals. The suspension of coated drug particles was continuously flushed out through the shell-side outlet of the PHFAC module into a microfiltration device (Omnipore Membrane JHWP09025, PTFE, hydrophilic, 0.45 μm, 90 mm; Millipore, Billerica, Mass.) to collect the encapsulated drug particles from the slurry. Products were vacuum dried and subjected to various characterization steps.

The sequence of pumping is important because the anti-solvent water must permeate through the pore first; otherwise, the viscous polymer solution can permeate to the tube side due to a pressure difference. There are at least three reasons for selecting the relatively high levels of the flow rate levels used in most of the experiments (e.g., 11 mL/min for the tube side water flow rate and 6 mL/min for the shell side flow rate of the drug-polymer solution). Firstly, the high flow rates aid in generating sufficient pressure in the tube side for DI water to permeate through the pores in the wall of the hollow fibers. Secondly, the velocity of the water streams emanating from the pores should be high enough to facilitate intensive mixing of the drug-polymer solution and the anti-solvent. Thirdly, after precipitation of both the drug particles and the polymer from the solution in the shell side, high levels of precipitation can create blockages in the shell side even with a relatively smooth FEP shell surface. The high flow rates of the incoming water streams and the acetone-based feed solution advantageously flush out the coated drug particles formed as well as any excess polymer precipitation so that the module can be run continuously to maximize productivity. It is also noted that the addition of a large excess of the anti-solvent water generated a very high level of supersaturation to precipitate the maximum amount of the drug and polymer.

v. Characterization Methods

A scanning electron microscope (LEO 1530 Gemini, Zeiss, Thornwood, N.Y.) was used to determine the morphology and particle surface structure for both uncoated and coated Griseofulvin. For sample preparation, a small amount of particle powder was placed on top of the pin stub mount. Carbon coating of the sample is necessary to make the sample sufficiently conductive and prevent distortion of the SEM micrographs due to charging of the specimen.

A thermogravimetric analyzer (Pyris 1, PerkinElmer, Waltham, Mass.) was used to obtain the weight of the polymer coating on the drug crystal since the polymer will decompose over a contain temperature range when heated up. Mass loss in that range will be the mass of polymer coating on the host particles. A dry uncoated/coated sample was placed on a hangdown pan inside of the instrument. The furnace temperature was increased from 50° C. to 550° C. at a rate of 10° C./min.

An X-ray diffractometer (Empyrean, Phylips, Westborough, Mass.) was utilized to measure the X-ray diffraction patterns of uncoated and coated GF powder samples. The operating voltage and amperage were 45.0 kV and 40 mA, respectively. About 100 mg of dry powder particles was gently placed on a sample holder; the surface of the sample was pressed by a glass to maintain co-planarity in the area. The scanning range was set from 5° to 45° 2θ at a step size of 0.02° 2θ and 15° time per step under the scanning of 255 detecting channels.

Dissolution tests for the uncoated and coated Griseofulvin particles were determined via a Distek dissolution tester (North Brunswick, N.J.). According to the USP II paddle method, 0.27% of SDS solution with 900 mL volume was added into the vessel as a buffer solution. Temperature of the medium was maintained at 37° C. and a paddle stirring speed of 50 rpm was used. The sample used was equivalent to a dose of 35 mg of GF, and dropped into a dissolution vessel containing the buffer solution. Samples having a volume of 6 mL were taken out at 1, 3, 5, 10, 20, 30, 40, 50 and 80 min and immediately analyzed by UV spectroscopy (52100UV+, Cole-Parmer, Vernon Hills, Ill.) at a wavelength of 296 nm. As a blank benchmark for the test, a 0.27% SDS buffer solution was measured first.

Differential scanning calorimetry (DSC 7, Perkin Elmer, Waltham, Mass.) was used over a temperature range of 30-250° C. at 10° C./min heating rate to measure the heating profile. About 3 mg of the sample was placed in an open pan under heating. The melting point of the sample was detected and calculated by Pyris software.

A Raman microscope (DXR, Thermo scientific, Waltham, Mass.) was applied to measure the molecular structure of the uncoated and coated GF particles in order to identify whether the coating of drug particles affected the drug composition. The laser power of the analyzer was set at 10 mw and the laser wavelength was 780 nm.

A laser diffraction particle size analyzer (LS230, Beckman Coulter, Brea, Calif.) was used to identify the extent of particle agglomeration. An aqueous micron-size suspension of the particle sample was prepared after 30 s of sonication to break the soft bonding between particles. After that a few drops of the suspension were introduced in the inlet of the instrument for analysis.

vi. Results and Discussion

1. Crystallization of Griseofulvin Drug Particles in PHFAC Unit W/Wo Polymer

Dry GF powder as received was first analyzed by SEM without any treatment. FIG. 3A shows a micrograph of pure GF particles at a given magnification. The surface of the drug particles as received appears to be very rough with a non-fractural structure; the particle size of GF is close to 10 μm. To find out whether the PHFAC process affects the characteristics of the drug particles compared to the drug particles as received, pure GF crystals were formed using the PHFAC process without the presence of any polymer. Drug particles were first fully dissolved into an acetone solution in a flask under stirring. The solution was directly passed through the shell side of the PHFAC device without any addition of Eudragit RL 100 while water was introduced from the tube side as the anti-solvent. The product was collected at the outlet in the other end on a filter paper and subjected to SEM characterization.

FIG. 3B shows the SEM micrographs of pure drug particles after pumping through the PHFAC device without any polymer. Compared to FIG. 3A where the GF particle hardly shows any crystalline shape, drug particles in FIG.

3B have a well-defined crystal structure. The surface is much smoother with only some tiny crystals attached to it. This is because the drug was first fully dissolved in acetone (0.55 g GF in 20 mL acetone); the GF particles precipitated out from the solution as a result of rapid solubility reduction in the PHFAC device.

2. Synthesis of Eudragit-Coated Griseofulvin Drug Particles in a PHFAC Unit

When the acetone solution containing both dissolved drug molecules and the polymer was pumped through the PHFAC crystallizer with the antisolvent water coming in from the tube side, it appears that the drug molecules crystallize rapidly from the solution first; then the polymer precipitates and coats the drug crystals. In FIGS. 3C and 3D, a thin polymer coating film can be seen on each drug crystal. Compared to FIG. 3B in which the drug particles were crystallized without the presence of any polymer, the surface morphology appears to be different. However, the polymer appears to have encapsulated the entire drug crystal.

3. Residence Time Variation

Residence Time plays an important role in the PHFAC process since precipitation of both the polymer and the drug can be affected by the variation of residence time in the shell side of the module. Residence time can be simply altered by changing the shell-side feed solution flow rate. To identify the influence of the feed solution flow rate on the particle size distribution (PSD) of GF crystals, the solution containing the dissolved drug without any polymer was passed through the PHFAC module at different rates. The particle size distribution will be affected by the extent of supersaturation created and the rate at which supersaturation is created. Both are influenced by the rate at which the anti-solvent is introduced from the tube side to the shell side for a given feed solution flow rate.

Results of the PSD of the drug crystals under different combinations of flow rates of the two streams (X0, X1, X2, and X3) are listed in Table 1. The combination X0 has the lowest tube side anti-solvent flow rate and the highest shell-side feed flow rate, which reduces the level of interaction between the feed and the anti-solvent to the lowest level. As a result, the combination X0 has the lowest extent of supersaturation and rate of supersaturation development: the median particle size of drug crystals is only 1.617 μm (FIG. 3E). Also, the recovery rate of the drug crystals is the lowest among all four conditions since most of the drug was still dissolved in the solution without precipitation. If the tube side anti-solvent flow rate is maintained at the same level but the shell-side feed solution flow rate is decreased to 6 mL/min (combination X1), the median particle size increased to 7.333 μm. This is due to an increase in the feed solution residence time which allows for more GF crystal growth time and consumption of the supersaturation created.

TABLE 1

The PSDs of drug crystals from PHFAC module without any polymer in the feed solution for various flow rates of the feed solution and the anti-solvent stream

| Experimental run | Shell side flow rate (mL/min) | Tube side flow rate (mL/min) | Median size (μm) | $d_{10}$ (μm) | $d_{90}$ (μm) |
|---|---|---|---|---|---|
| X0 | 11 | 6 | 1.617 | 1.001 | 2.219 |
| X1 | 6 | 6 | 7.333 | 4.977 | 15.29 |
| X2 | 6 | 11 | 11.83 | 2.117 | 30.30 |
| X3 | 12 | 11 | 11.76 | 2.939 | 26.62 |

For flow combinations of X2 and X3, the tube side anti-solvent flow rate was increased from 6 to 11 mL/min giving rise to intensive mixing of the feed solution with the anti-solvent resulting in rapid development of very high levels of supersaturation. When comparing the combination X3 with the combination X2, it appears that in spite of doubling the shell side feed flow rate, the median size of particles still remained essentially the same. It is possible that with such a high tube side flow rate, the rate of supersaturation development and the growth rates are high enough to allow for ample growth of the drug particles. Further the shell-side residence time variation employed was not high enough to affect the final PSD of the drug particles. In addition, it appears that the drug was fully precipitated from the solution and grew to its maximum size.

It is clear that the drug crystal size can be altered by variation of both the feed solution flow rate and the tube-side anti-solvent flow rate. Polymer coating experiments were also performed under these conditions to show that after the drug crystal size was controlled by varying the residence time, the drug crystals can still be coated with polymer that precipitated in the PHFAC module. FIG. 3E shows an SEM micrograph of uncoated crystals prepared under the flow-rate combination X0 involving the smallest residence time and the lowest extent of supersaturation (Table 1) while FIG. 3F shows the SEM micrograph of a coated GF crystal obtained under the combination X1 (Table 1).

It is important to know the sequence and extent of co-precipitation of the drug and the polymer when introducing the anti-solvent from the tube side of the PHFAC module. If the drug particles precipitate/crystallize first, then the final product is most likely to be polymer-coated drug particles. However, if both the drug and the polymer crystallize or precipitate at the same time, the product will be either the drug dispersed in a polymeric matrix or vice versa leading to a matrix product for controlled release. For a preliminary exploration of this aspect, another experiment was run under the flow-rate combination of X1 (Table 1). However, the only difference with X1 is that the acetone solution on the shell side had pure Eudragit RL 100 polymer; the drug Griseofulvin was not present in the feed solution.

After the PHFAC process was implemented, no polymer precipitate was collected on the filter paper from the module outlet. This suggested that the rate of polymer precipitation in the absence of the drug crystals was zero for the low residence time used and the extent of anti-solvent induced supersaturation created. The polymer appears to precipitate rapidly only in the presence of crystals of drug particles which serve as nuclei for polymer crystallization. As a result, when the polymer solution containing dissolved drug molecules was pumped into the PHFAC unit, the drug crystals appeared first out of the solution due to supersaturation induced by the anti-solvent; then the polymer underwent heterogeneous nucleation and covered the GF particles. Subsequently, the products of polymer coated GF particles were collected on the filter paper.

4. Particle Size Distribution

Since one of the objectives of the study is to understand the impact of this novel PHFAC coating technique on the synthesized drug particles, the as-received uncoated GF particles and the Eudragit-coated GF particles obtained from the PHFAC were selected for particle size distribution analysis. A suspension of the samples in water was carefully dropped into the inlet of the laser diffraction particle size analyzer. Results of the two samples are shown in FIG. 4. The median size of the uncoated GF sample (11.6 μm) was close to the manufacturer's specification (10 μm). After polymer coating, the median size of the coated drug particles increased to 19.2 μm. One reason for the median size increase is obviously due to the coating which increases the particle size. Another reason is that the coating of GF by the polymer brings in a certain amount of agglomeration. Attachment of neighboring coated drug particles will take place due to the sticking tendency of the polymer-formed liquid bridges.

5. TGA Characterization of Polymer Coated Drug Particles

As a precise thermal analysis method, thermogravimetric analysis (TGA) is used to determine the percent weight loss of the sample as a function of increasing temperature. TGA can be used in the case of polymer coated drug particles to measure the weight of the polymer coating if we can identify the different temperature ranges over which weight loss is caused by either drug decomposition or polymer decomposition when heated up.

Figure 5:
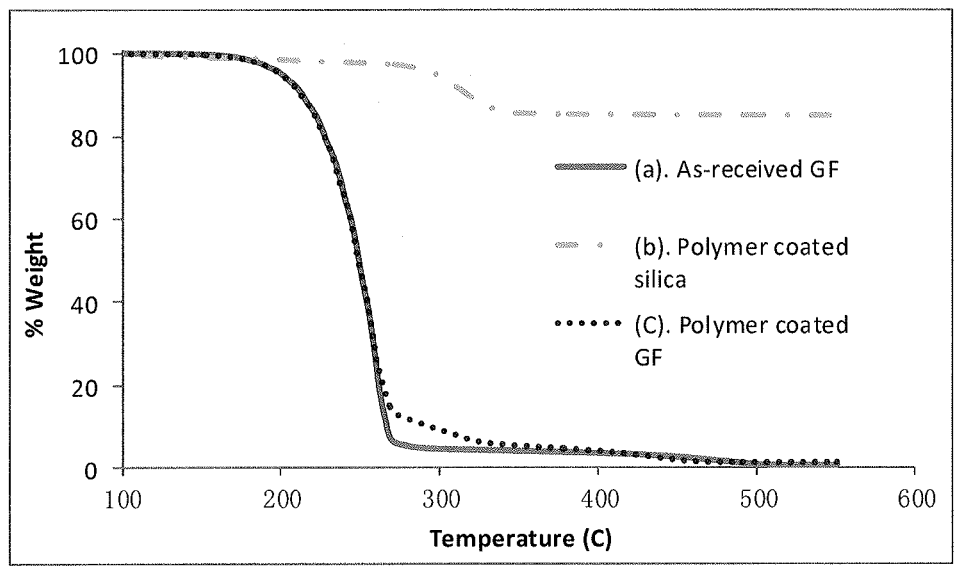
FIG. 5 is a plot of thermogravimetric analysis (TGA) results of as-received GF, polymer-coated GF and polymer-coated silica particles.

A small amount of pure GF particles was placed in a hangdown pan inside the TGA analyzer where the temperature was increased from 25° C. to 550° C. at a rate of 10° C./min. In FIG. 5, line (a) illustrates the TGA result for a pure GF sample. The drug will start decomposing when heated up with most of the weight loss happening between 150 and 260° C., suggesting this to be the temperature range over which Griseofulvin decomposed.

In FIG. 5, line (b) illustrates the TGA result for Eudragit RL 100 coated silica from previous experiments. Since silica particles do not decompose even when the temperature goes up to 550° C., the percent weight loss is essentially due to the loss of the polymer. The region of polymer decomposition is roughly between 200 and 450° C. Therefore, the overlapping temperature range between the drug decomposition and the polymer decomposition is between 200 and 260° C. From the TGA profile of line (b) in FIG. 5 valid for the polymer coated silica particles, about 20% of the polymer decomposed in the range of 200-260° C. Therefore, in the case of the polymer-coated drug, the polymer-based weight loss of the sample from 200 to 260° C. may be expected to be one fourth of the weight loss of the sample between 260-550° C. Line (c) in FIG. 5 shows the TGA results for the polymer coated drug particles. The weight loss % of the polymer can be estimated as follows:

$$M_{Polymer\ weight\ loss} = M_{260-550} + M_{200-260} = M_{260-550} + 0.25 \times M_{260-550} = 1.25 \quad (Eq.\ 1)$$

$M_{260-550}$ =12.5% of the total weight loss (from line (c) in FIG. 5)

That means about 12.5% of the weight of the whole sample was due to the amount of polymer coating over the drug particle.

Assuming that every drug crystal is a rectangular parallelepiped having dimensions of $H_{drug}$, $W_{drug}$ and $L_{drug}$ with a polymer coating of uniform thickness h covering the entire drug crystal, the equation governing the relationship between the mass of the polymer coating and that of the drug particle being coated is obtained as follows:

$$\frac{m_{drug}}{m_{polymer}} = \frac{\rho_{drug} H_{drug} \times W_{drug} \times L_{drug}}{\rho_{polymer}[(H_{drug}+2h) \times (W_{drug}+2h) \times (L_{drug}+2h) - H_{drug} \times W_{drug} \times L_{drug}]} \quad (Eq.\ 2)$$

where $m_{drug}$ and $m_{polymer}$ are respectively the mass of the GF particles and the polymer based on the TGA results. The densities of the host drug particles and polymer are $\rho_{drug}$ (=1.4 g/ml) and $\rho_{polymer}$ (~1.1 g/ml), respectively. The length, width and height of the drug crystals are estimated to be 10 μm, 2 μm and 2 μm based on the SEM micrograph-based results (see FIG. 3C). The polymer coating thickness, h, was estimated from equation (2) above to be 0.075 μm.

6. XRD and Raman Results.

Figure 6A:
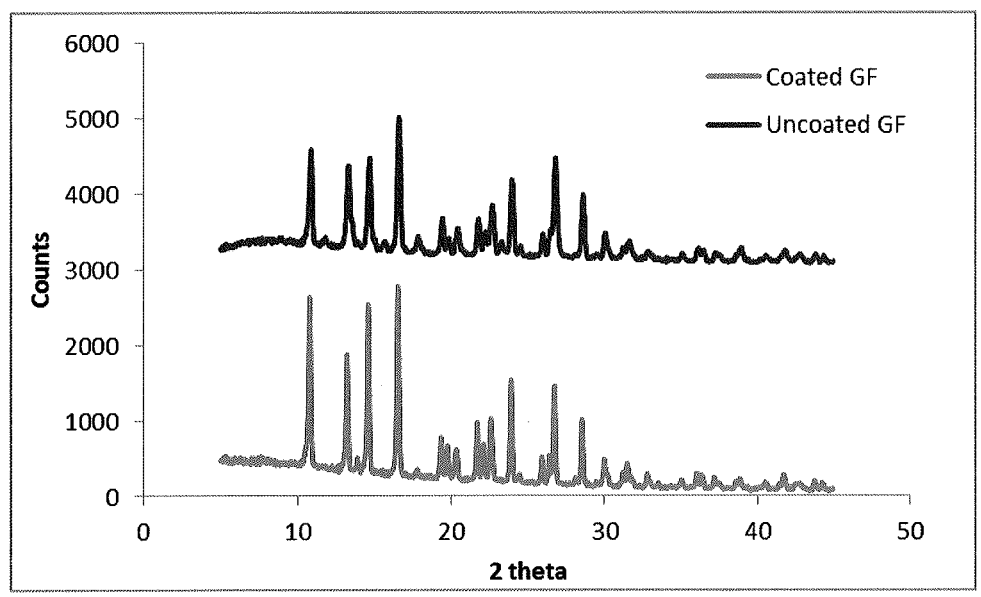
FIG. 6A is an X-ray diffractograms of uncoated GF and coated GF samples.
Figure 6B:
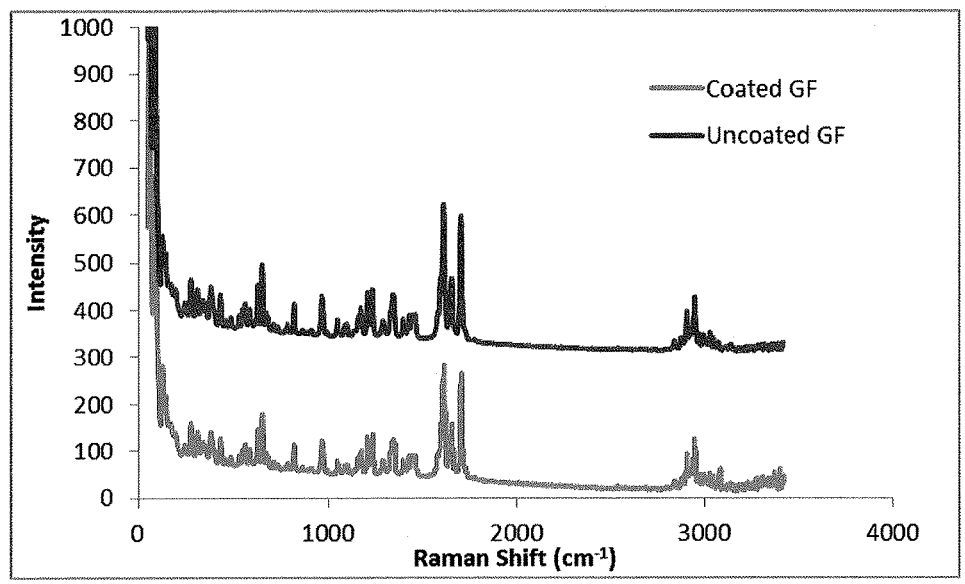
FIG. 6B is a Raman spectra for uncoated GF and coated GF samples.
Figure 7:
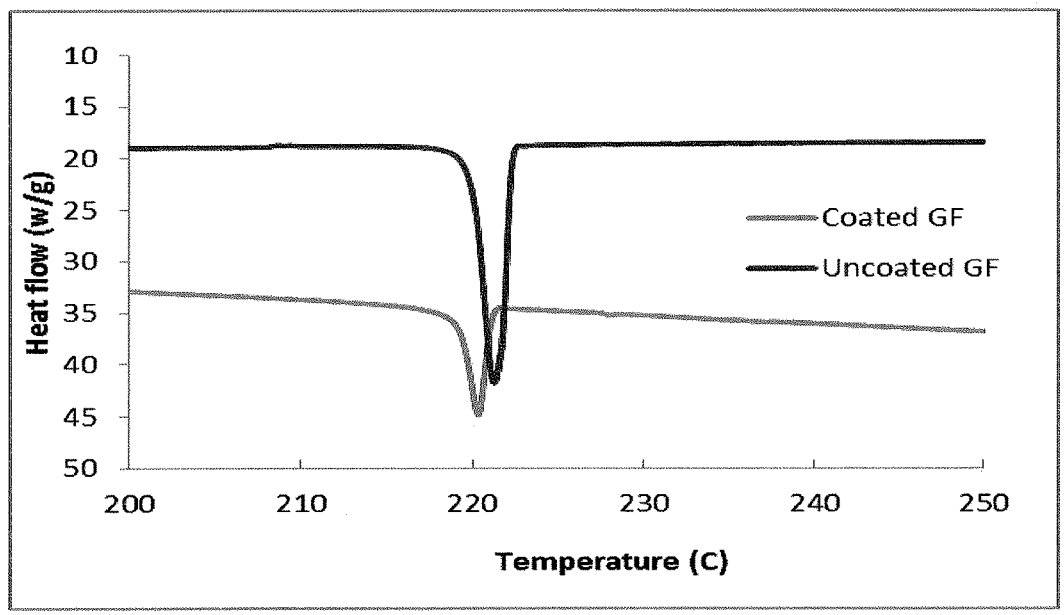
FIG. 7 depicts differential scanning calorimetry patterns for uncoated GF and coated GF.
Figure 8:
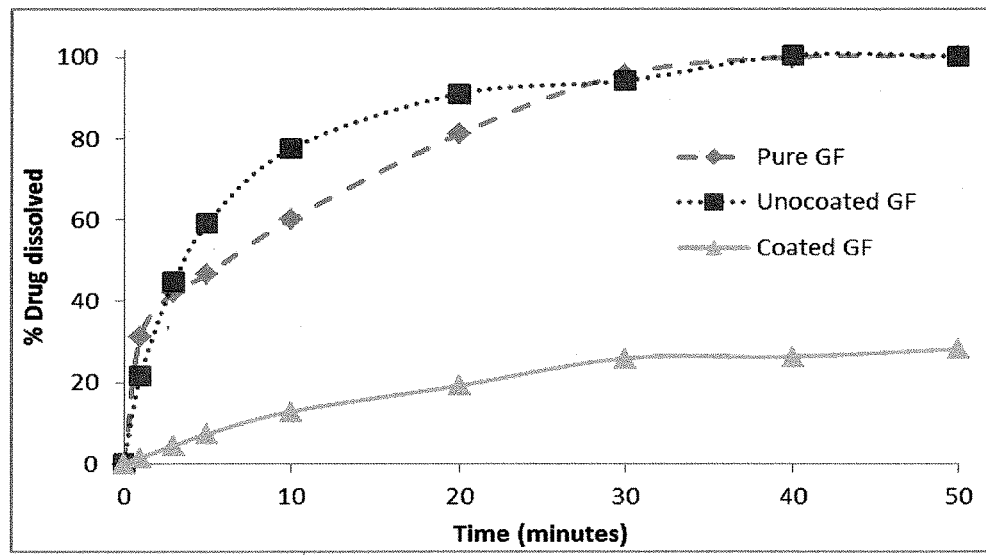
FIG. 8 depicts dissolution profiles for crystals of pure GF (as supplied), uncoated GF and polymer coated GF, the latter two obtained by the PHFAC technique.

Flattened powder format of the uncoated GF crystals and polymer coated GF crystals was prepared and analyzed by x-ray diffraction (XRD) to identify whether the coating of the drug crystals by the PHFAC process will damage the crystal structure of GF. As can be seen from the XRD results in FIG. 6A, both uncoated and coated GF patterns show no alteration in the peak position. The characteristic peaks of both samples are identical. FIG. 6B illustrates the Raman spectra results for uncoated and coated GF crystals at the Raman shift range from 0 to 4000 $cm^{-1}$. Identical peaks for both uncoated GF and the polymer-coated GF proved that during the anti-solvent crystallization, even though the GF drug has crystallized from a solution containing the dissolved polymer and has been coated by the polymer, molecular structure remained unaffected. Raman spectra were in accordance with the XRD results in FIG. 6A.

7. Differential Scanning Calorimetry (DSC)

DSC patterns for as-received GF and the polymer-coated GF are shown in FIG. 7. In the thermogram, the peak starting position implied the melting point of pure Griseofulvin to be 219.97° C. This peak position is comparable to the pattern for polymer coated Griseofulvin which has the value of 219.22° C. The intensity difference may be attributed to the coating covering the drug particles; it is likely to attenuate the signal strength. The very close (almost identical) positions of the peaks in either XRD or DSC diagram suggest that the polymer coating by the anti-solvent crystallization process did not alter the crystallinity of the drug Griseofulvin.

8. Dissolution Test

To illustrate the advantages of a coated drug for controlled release, dissolution tests were performed on three samples: as-received drug, uncoated drug, and polymer-coated drug. FIG. 8 shows the dissolution profiles for the three samples up to 50 minutes. The uncoated GF and the as-received GF have essentially similar dissolution curves. These results show that even after being pumped through the SHFCC device and crystallized by the PHFAC process, the uncoated GF crystals will dissolve with time in a manner similar to that for the as-received drug. On the other hand, only about 20% of the polymer coated GF dissolved even after 50 minutes, which suggests that the coating is effective in achieving controlled release of GF.

c. Experimental Testing/Results—Experiment #2 i. Materials

Host submicron silica particles, Cosmo 55 (550 nm nonporous hydrophilic spherical particles), were obtained from Presperse (Somerset, N.J.). Silica nanoparticles used were Aerosil 200 (non-porous hydrophilic fumed silica with a diameter of 12 nm) (Evonik-Degussa, Parsippany. N.J.). Coating polymers were: Eudragit RL 100 ($M_w$, 150,000; a copolymer of methyl methacrylate, ethyl acrylate and methacrylic acid ester) from Evonik-Degussa (Parsippany, N.J.); PLGA (Poly (D, L-lactide-co-glycolide), $M_w$ 7,000-17,000) from Sigma-Aldrich (St. Louis, Mo.). Acetone, a good solvent for Eudragit RL 100, dioxane, a good solvent for PLGA, and the surfactant sodium dodecyl sulfate (SDS), were obtained also from Sigma-Aldrich. Deionized water was used as the anti-solvent.

ii. Experimental Methods

Feed solution-suspension was prepared in a flask by first introducing 2.4 g of Eudragit RL 100 (or PLGA) in 20 ml acetone (or dioxane) solution. After about 30 minutes when the polymer was fully dissolved, 4 ml of water was added in the solution to slightly decrease the solubility of the polymer. This was done to make the polymer solution more sensitive to the anti-solvent. Next, 0.4 g of Cosmo 55 silica particles was added along with 0.025 g of SDS. The flask was placed under a magnetic stirrer and kept stirred during the experiment.

Figure 2D:
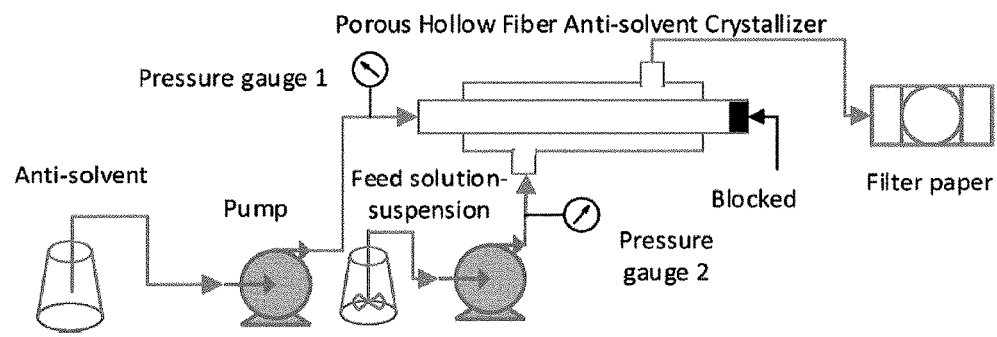
FIG. 2D provides a schematic depiction of an experimental setup for an exemplary porous hollow fiber anti-solvent crystallization/coating system for continuous coating of particles according to the present disclosure.
Figure 4:
FIG. 4 is a plot of particle size distribution for uncoated GF and coated GF under PHFAC.
Figure 4:
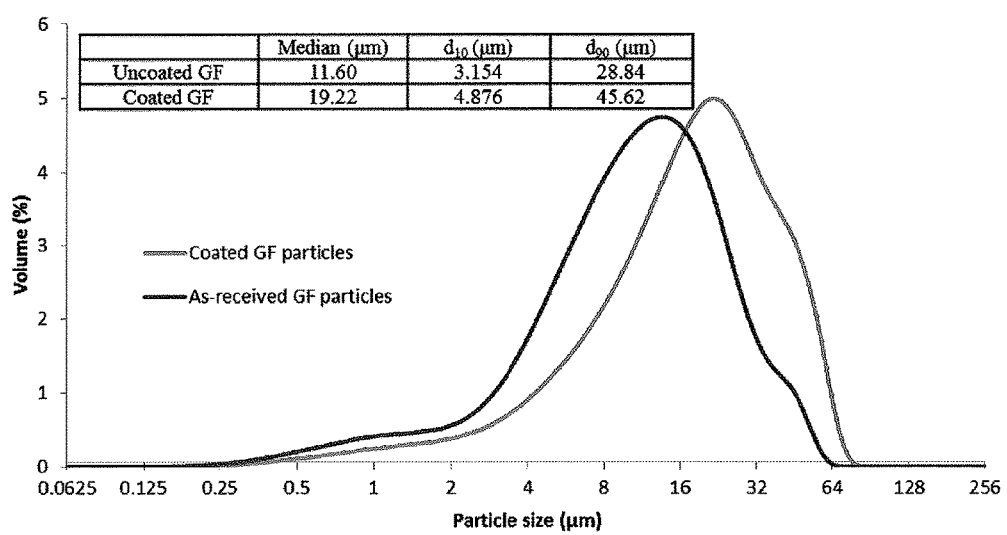

FIG. 2D illustrates the process schematic used for the PHFAC-based coating of the silica particles. A peristaltic pump (Masterflex L/S model 7518-60, Cole-Parmer, Vernon Hills, Ill.) was used first to pass DI water to the tube side of the module. Since the other end of the module tube-side was blocked by a valve, tube side pressure increased from 0 to 15 psig so that the water permeated through the pores in the hollow fiber wall to the shell side. The feed solution-suspension was introduced into the shell side of the PHFAC unit by another identical pump after 2 minutes.

The order of pumping the liquids should not be reversed. If the feed solution were first passed to the shell side, then part of this solution would have permeated to the lumen side which would have led to subsequent mixing of the anti-solvent with the polymer solution and the precipitated polymer would have stayed in the tube, eventually leading to clogging of the tube side. The reading on the pressure gauge 2 (FIG. 2D) was close to zero psig since the volume of the shell side is relatively large, offering the solution almost no resistance to pass through. Innumerable water streams from the pores were injected into the feed polymer solution-suspension in the shell side generating strong mixing of the solutions. The solubility of the polymer drastically deceased because of the introduction of the anti-solvent so that the polymer precipitated and covered the silica host particles. The coated product along with the excess polymer solution and water were continuously pumped out through the shell side outlet. A microfiltration device was placed under the outlet to collect the particles on a filter paper (Omnipore Membrane JHWP09025, PTFE, hydrophilic, 0.45 μm, 90 mm; Millipore, Billerica, Mass.). The coated silica particles were recovered from the filter paper and vacuum dried to make them ready for characterization.

The flow rate on the hollow fiber lumen side was kept at 11 ml/min and the shell side flow rate was maintained at 6 ml/min. It is important to maintain a reasonable flow rate in the shell side. First, a polymer such as PLGA is highly sensitive to the anti-solvent; the presence of just a little anti-solvent in the shell side will lead to extensive precipitation of the PLGA. Unless the shell-side flow rate is high enough to flush out the precipitates once they are formed, the precipitates can block the shell side. Secondly, the shell side flow rate is related to the pressure in the tube side. The shell side flow rate has to be held at a certain level to increase the pressure difference between the tube side and the shell side so that the anti-solvent water can successfully permeate from the tube side to the shell side and achieve intense mixing with the feed solution-suspension. One can generate a high super-saturation level if a high water flow rate is created so that a maximum amount of the polymer can be crystallized out without any waste.

iii. Characterization Methods

A scanning electron microscope (LEO 1530 Gemini, Zeiss, Thornwood, N.Y.) was employed to determine the surface morphology of the polymer coated silica particles. The dry powder sample was placed in a standard SEM pin stub mount. Since the specimen has poor electrical conductivity, carbon coating of the sample has to be performed to eliminate charging of the sample. Energy-dispersive X-ray spectroscopy (EDS) was also used for elemental analysis of any sample. Uncoated silica particles have only silicon and oxygen elements. After polymer coating of the submicron particles or nanoparticles of silica, the element carbon should be detected on the sample by EDS since both the polymers Eudragit and PLGA in the coating contain carbon.

A thermogravimetric analyzer (Pyris 1, PerkinElmer, Waltham, Mass.) was utilized for measurement of the weight of the polymer coating. Since silica particles do not lose weight during heating up, the percent weight loss will reflect the loss of the mass of the polymer coated on the silica particles so that the coating thickness can be estimated. The sample was placed on a hang down pan inside the TGA chamber. The temperature was first kept at 50° C., and then the temperature was increased to 550° C. at a rate of 10° C./min.

A laser diffraction particle size analyzer (LS 230, Beckman Coulter, Brea, Calif.) was used to determine the particle size distribution. An aqueous particle suspension of the particle sample was prepared by introducing the dry sample powder into DI water and sonicating it for about 30 seconds to break the soft bonding.

iv. Results and Discussion:

1. Coating of Submicron Silica Particles with Eudragit RL 100

Submicron silica particles (Cosmo 55, 550 nm) were first coated with the polymer Eudragit RL 100. The polymer was precipitated in the PHFAC module due to the rapid solubility reduction when DI water was introduced from the tube side thus coating the silica host particles. Eudragit RL 100 is not as sensitive to the anti-solvent water compared to PLGA. Even when a considerable amount of water was quickly introduced into a solution of Eudragit, limited precipitation occurred; the color of the solution changed from clear to slightly cloudy per visual inspection. Therefore, a high concentration of polymer (10 wt %) as well as a high water permeation rate from the tube side must be maintained to ensure sufficient polymer precipitation on the silica particles.

It appears that the quantity of the host silica particles plays an important role in determining the coating thickness since the polymer concentration of the solution was fixed. Other conditions remaining fixed, the magnitude of the residence time of the feed solution-suspension in the shell side essentially determines the amount of the polymer that will precipitate. Therefore, the higher the number of host particles present in the solution, the lower will be the amount of polymer that will precipitate on each silica particle and coat it. To that end, three identical Eudragit solutions were prepared containing exactly the same amount of water, acetone, polymer and SDS; the only difference between these solution-suspensions being the amount of silica added (0.2 g, 0.4 g and 0.8 g).

Figure 9:
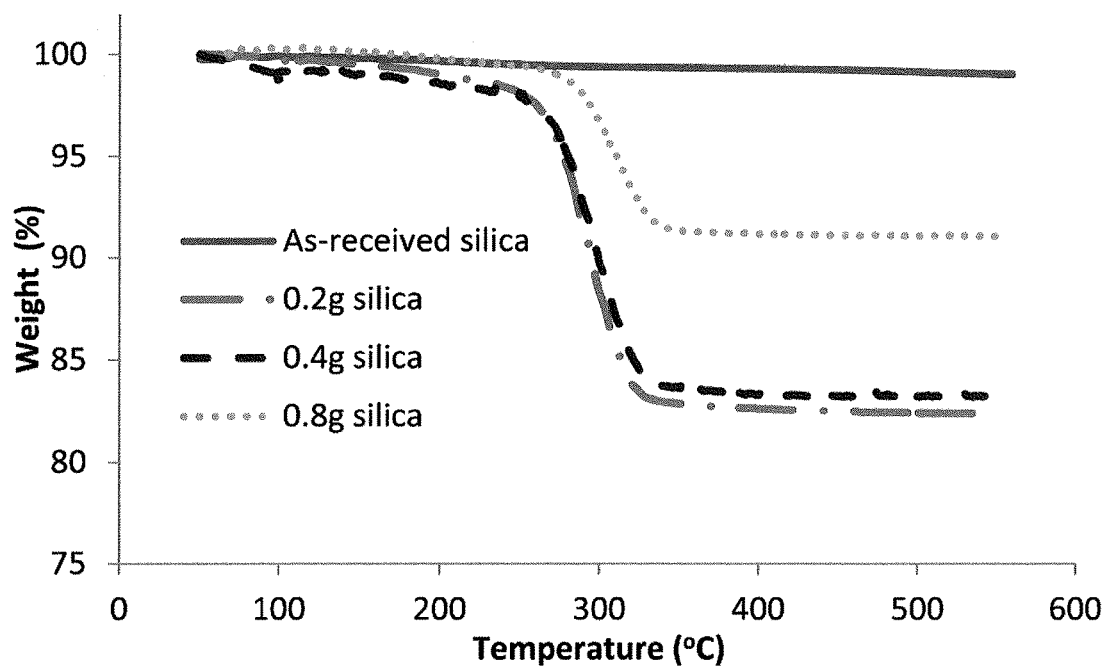
FIG. 9 provides TGA micrographs of as-received silica (Cosmo 55) as well as Eudragit RL 100 coated silica particles under different feed conditions.

Thermogravimetric analysis (TGA) was used to analyze the weight loss of the polymer-coated silica particles. The polymer coating that covered the silica particles started decomposing gradually during heating resulting in a weight loss of the sample. FIG. 9 illustrates the TGA results for coated Cosmo 55 particles for three different amounts of silica in the feed solution-suspension and the uncoated Cosmo 55 particles as received. The as received silica sample lost less than 1% of its weight after heating (the solid line in FIG. 9). This suggests that the weight loss of the coated silica samples was essentially due to polymer loss. According to the TGA results, the % weight loss decreased when more silica was added to the solution implying a thinner coating on the silica particles. The % weight losses for the cases of 0.4 g silica and 0.2 g silica addition are relatively close implying that the amount of polymer that can be deposited on the silica particles has an upper limit. Most of the experiments were therefore run with 0.4 g as the mass of silica. A lesser amount of silica addition will lead to a somewhat thicker coating and potentially increase the agglomeration of the polymer coated particles. Too many silica particles may lead to thinner and deficient coating.

Since the as-received Cosmo 55 particles are almost perfectly spherical with a very narrow particle size distribution, these silica particles may be assumed to be spheres of diameter 2r. The relationship between the mass of silica and the polymer mass can be expressed as follows:

$$\frac{m_{Silica}}{m_{Polymer}} = \frac{\rho_{Silica} \frac{4}{3}\pi r^3}{\rho_{Polymer} \frac{4}{3}\pi\{(r+h)^3 - r^3\}} \quad \text{(Eq. 3)}$$

Here $m_{Silica}$ and $m_{Polymer}$ are the mass of the uncoated silica particle of radius r and the polymer present in the coating, respectively; the densities of the host silica particles and the polymer are $\rho_{Silica}$ (2.65 g/cm$^3$) and $\rho_{Polymer}$ (1.1 g/cm$^3$), respectively. The polymer coating thickness h can be calculated from equation (1) as $$h = r(1 + \rho_{Silica} m_{Polymer}/\rho_{Polymer} m_{Silica})^{1/3} - r = 36.9 \text{ nm} \quad \text{(Eq. 4)}$$

where the value of r used is 275 μm. In a number of studies conducted earlier, the estimates of coating thickness determined via equation (1) were found to be reasonable when compared with other direct estimates of the coating thickness.

2. Characterization by Scanning Electron Microscopy

Figures 10A, 10B:
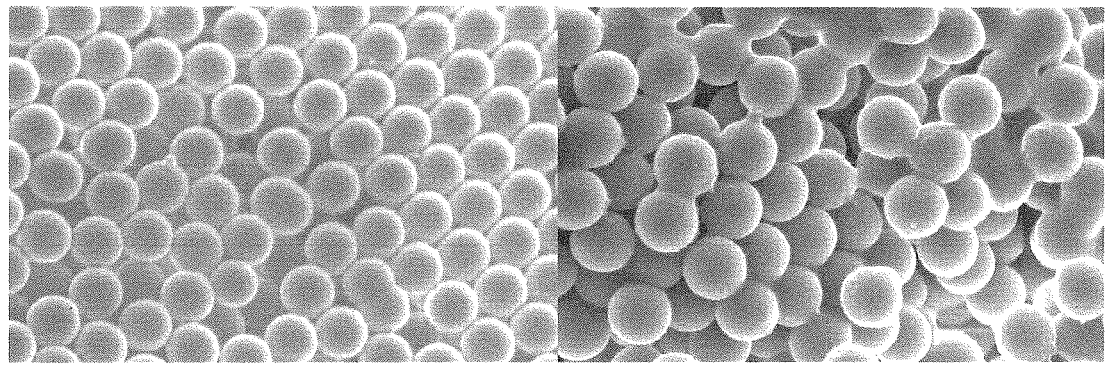
FIGS. 10A and 10B provide SEM micrographs.

After about 20 minutes of operation, a sample was obtained on the filter paper for characterization. SEM was used to detect the actual surface coating topography and composition of the polymer coated Cosmo 55 particles. FIGS. 10A and 10B show the SEM micrographs of uncoated and coated dry silica particles. Compared to FIG. 10A, FIG. 10B clearly shows that the polymer was coated on every silica sphere due to heterogeneous nucleation. Limited amounts of polymer bridges between neighboring silica particles suggest soft bonding or agglomeration between particles, which can be separated by the external forces experienced in an ultrasonicator to obtain free-flowing coated particles.

Figure 11A:
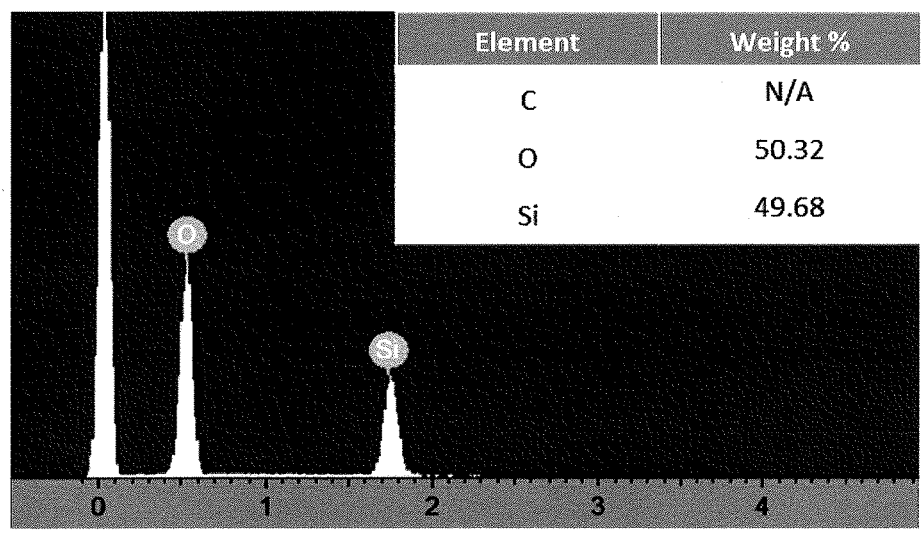
FIGS. 11A and 11B are EDS results of uncoated and Eudragit RL 100 coated submicron silica particles (Cosmo 55), respectively.
Figure 11B:
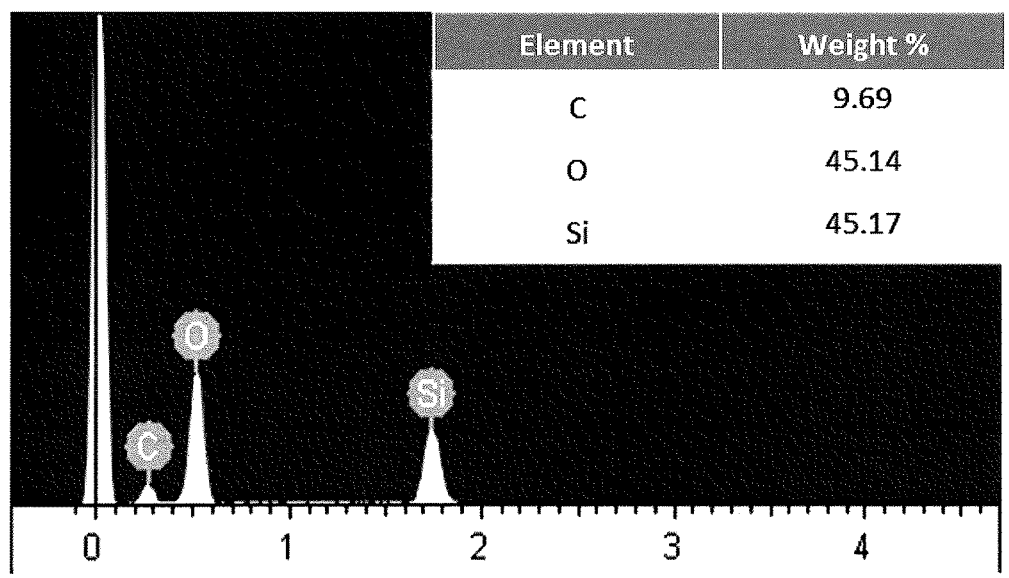

Surface elemental analysis by EDS can provide additional information of the composition of the coating on the silica particles. The EDS results of the uncoated and the coated Cosmo 55 samples are shown in FIGS. 11A and 11B, respectively. No carbon peak appears in FIG. 11A, suggesting that there was no carbon element on the as-received silica particles. On the contrary, a clear carbon peak shown in FIG. 11B indicates that Eudragit RL100 polymer successfully coated the Cosmo 55 silica particles since only the polymer contains the element carbon. The EDS results are in accordance with the SEM results.

3. Characterization by Scanning Transmission Electron Microscopy (STEM)

Figure 12A:
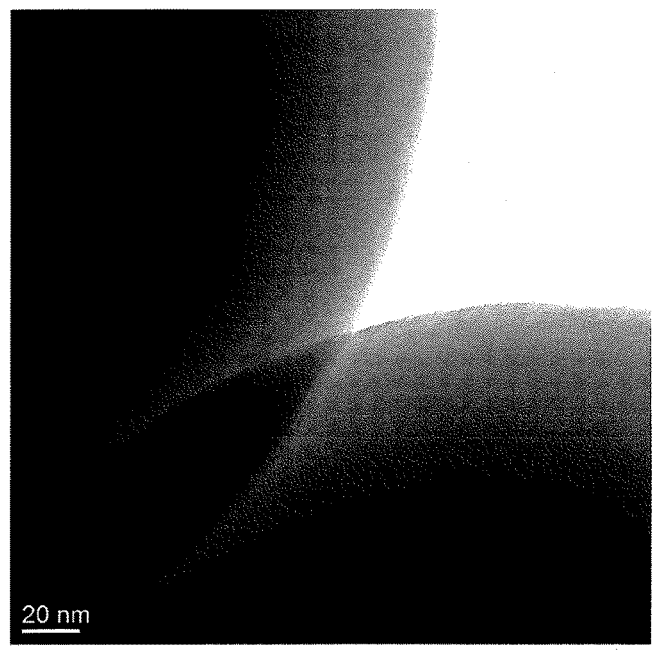
FIGS. 12A and 12B are STEM micrographs of uncoated silica particles and polymer coated silica particles after PHFAC process, respectively. Feed solution-suspension employed: 0.4 g silica, 2.4 g Eudragit RL, 20 ml acetone and 4 ml water.
Figure 12B:
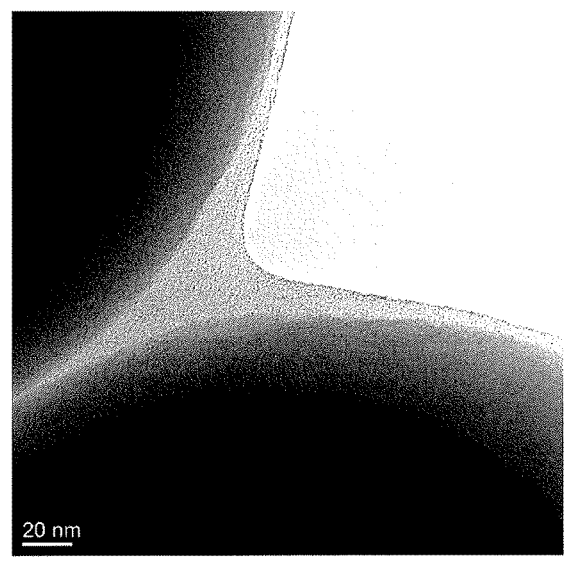

Scanning transmission electron microscopy (STEM) is another tool that can be used to determine the coating thickness of the polymer around the silica particles. Compared to SEM, STEM can display the coating morphology more precisely. The micrograph in FIG. 12A shows parts of two uncoated silica particles, while the micrograph in FIG. 12B shows sections of two Eudragit-coated silica particles. The two dark partial spheres in FIG. 12B represent two silica particles: the polymer coating covering the particles is shown in grey. The two silica particles in FIG. 12B are seen to be interconnected by a polymer bridge; a thin polymer coating is seen around the periphery of the particles. Based on the scale bar in the micrograph, the thickness of the coating on a single submicron silica particle is estimated to be between 10 nm and 20 nm.

4. Coating of Cosmo 55 Silica Particles with PLGA

PLGA is frequently used as a coating material in the pharmaceutical industry since it is a biodegradable and biocompatible copolymer approved by FDA. Compared to a solution of Eudragit RL 100 in acetone, a solution of PLGA in dioxane is much more sensitive to the addition of an anti-solvent such as water into the polymer solution than a solution of Eudragit RL 100 in acetone. High levels of precipitation will take place in the shell side if 10 wt % PLGA was added into solution. The PLGA concentration level can be a determining factor in the coating of submicron particles. Solutions having different concentrations of PLGA were therefore prepared to explore how the amount of PLGA will affect the coating since PLGA is much more sensitive to the anti-solvent compared with Eudragit RL 100.

Figure 13:
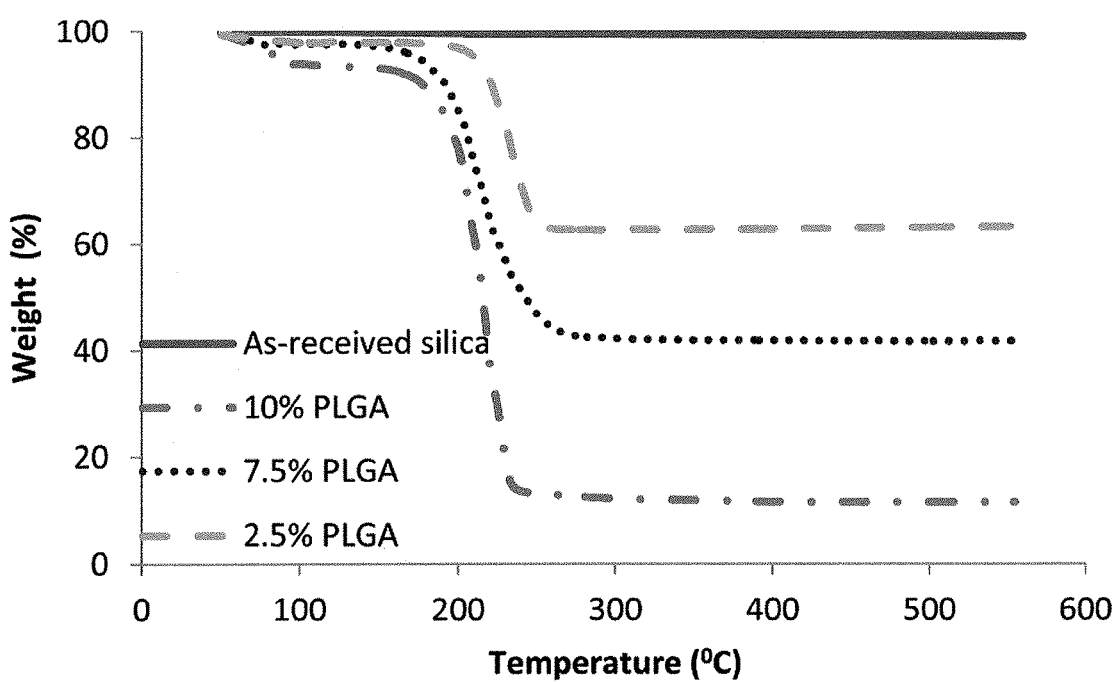
FIG. 13 is a plot showing the results from TGA of the as received (uncoated) silica particles and PLGA-coated silica particles.

FIG. 13 illustrates the results from TGA of the as received (uncoated) silica particles and PLGA-coated silica particles. As the solution PLGA concentration was increased, the amount of the precipitated polymer increased drastically, indicating that the extent of supersaturation of PLGA increased with the anti-solvent addition very rapidly and the precipitation kinetics was very fast. From the results of TGA, the percentage weight loss of the polymer were estimated to be 90%, 60% and 37% corresponding to PLGA concentrations in the solutions of 10%, 7.5% and 2.5% respectively. These extraordinarily high amounts of precipitation demonstrate the sensitivity of the dioxane solutions of PLGA used in this study to the addition of the anti-solvent water. Unlike coating with Eudragit RL 100, when the PLGA solution was mixed with the anti-solvent jet streams in the PHFAC module, PLGA was fully precipitated out from the solution.

Figures 14A, 14B:
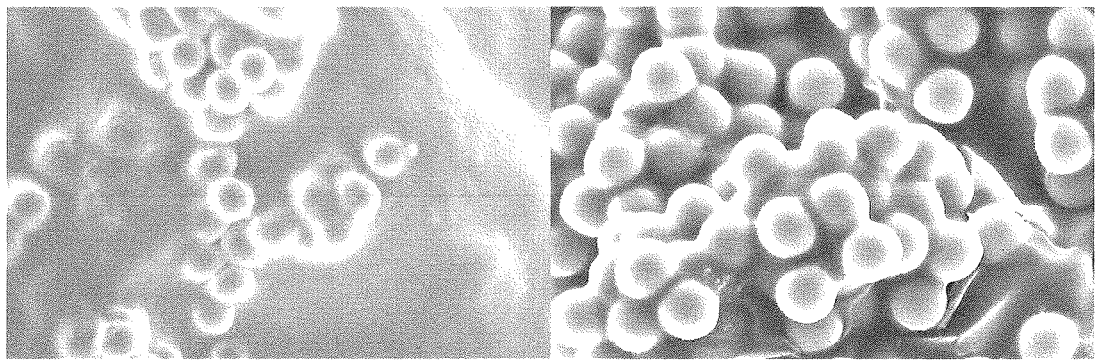
FIGS. 14A and 14B are SEM micrographs of PLGA coated particles from solutions containing two different levels of PLGA.

FIGS. 14A and 14B show SEM micrographs for polymer-coated silica particles from 10% and 2.5% PLGA solutions, respectively. In FIG. 14A, silica particles appear to be immersed in a huge amount of PLGA precipitate. However, for 2.5% PLGA solution, FIG. 14B shows that the silica particles had a thick coating and were somewhat interconnected but not embedded in the polymer matrix. This suggests that reduction of the solution concentration of PLGA can effectively decrease the coating thickness as well as the extent of agglomeration. Calculations using equation (3) suggest the thickness of the coating for 2.5 wt % PLGA solution to be 94 nm Since there were some polymer bridges between the particles, the real coating thickness along the particle periphery should be less than 94 nm.

Figures 15A, 15B:
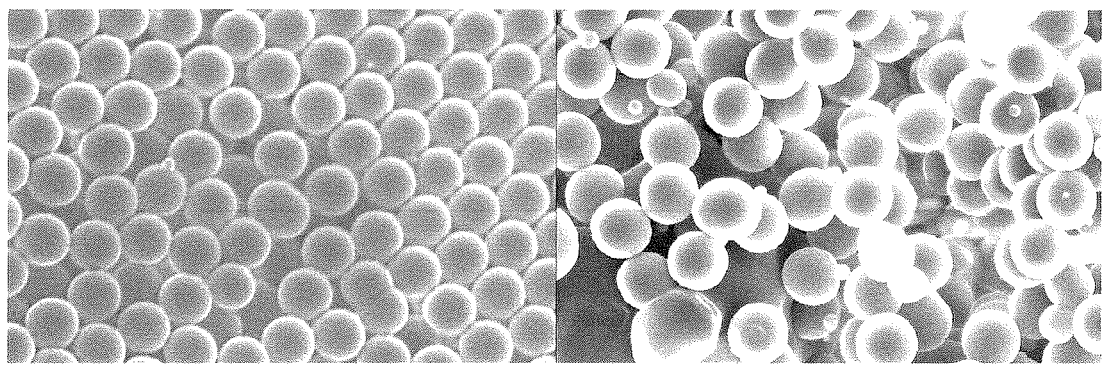
FIGS. 15A and 15B are SEM micrographs of uncoated and 1 wt % PLGA coated particles, respectively.

To assess whether further reduction of the solution concentration of PLGA could further reduce the amount of bridging and the coating thickness, reduced solution concentration was investigated. FIGS. 15A and 15B illustrates SEM micrographs of uncoated silica and PLGA-coated silica for the case of a 1% PLGA solution. There is very little difference between the two micrographs at the level of magnification used. Compared with the as-received Cosmo 55, the coating in FIG. 15B appears to be quite limited. The small amount of precipitation of PLGA was not enough to cover the particles; instead small amounts of polymer appear to be attached to the surface of some of the silica particles or lie in between particles. It appears that PLGA concentration cannot be reduced too much since it may result in an imperfect coating.

Figure 16A:
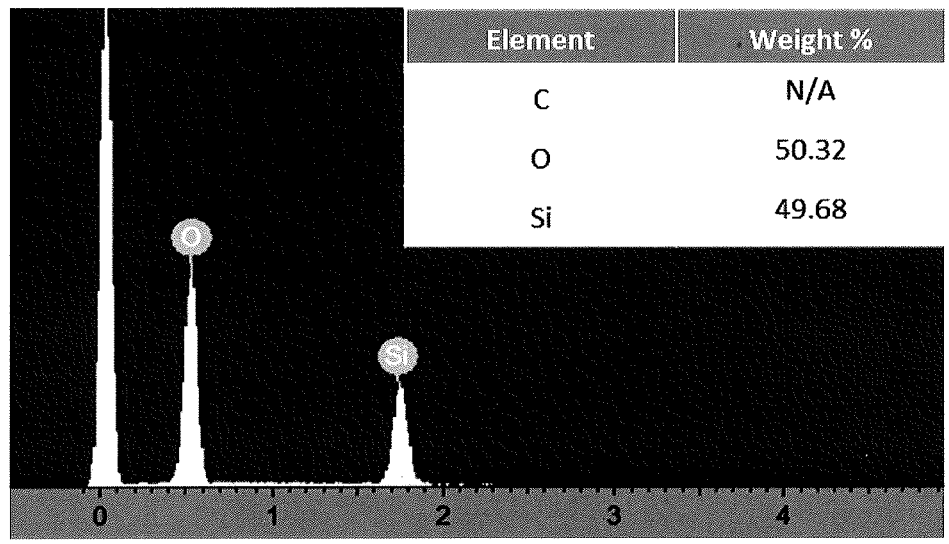
FIGS. 16A and 16B are EDS results of uncoated and PLGA coated Cosmo 55 submicron particles, respectively.
Figure 16B:
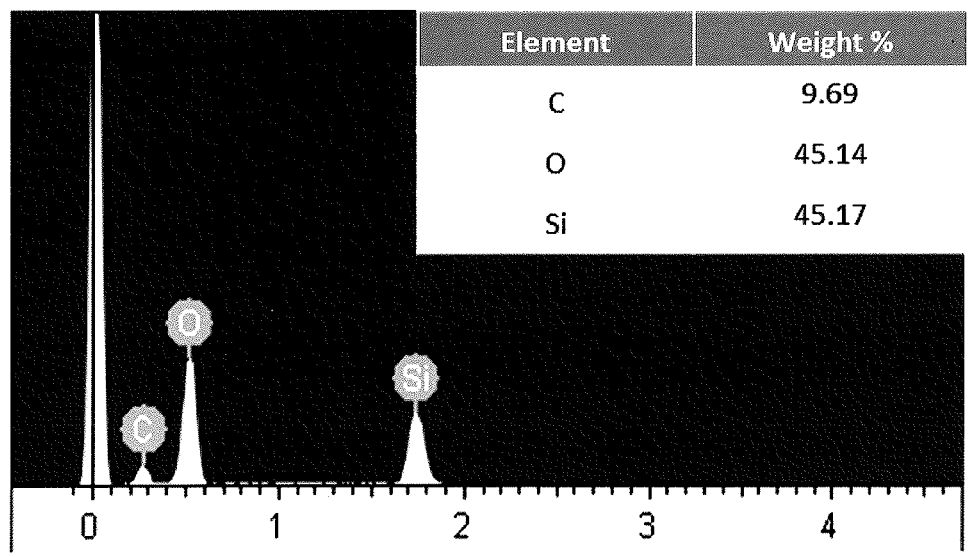

Therefore, the 2.5 wt % solution of PLGA was selected for further anti-solvent crystallization/precipitation experiments and characterization. The EDS results of uncoated silica as well as 2.5 wt % PLGA solution-based coated silica particles are shown in FIG. 11. As in FIG. 11B, the carbon peak in FIG. 16B demonstrates the existence of PLGA coating on the silica particles.

5. Particle Size Distribution

Figure 17:
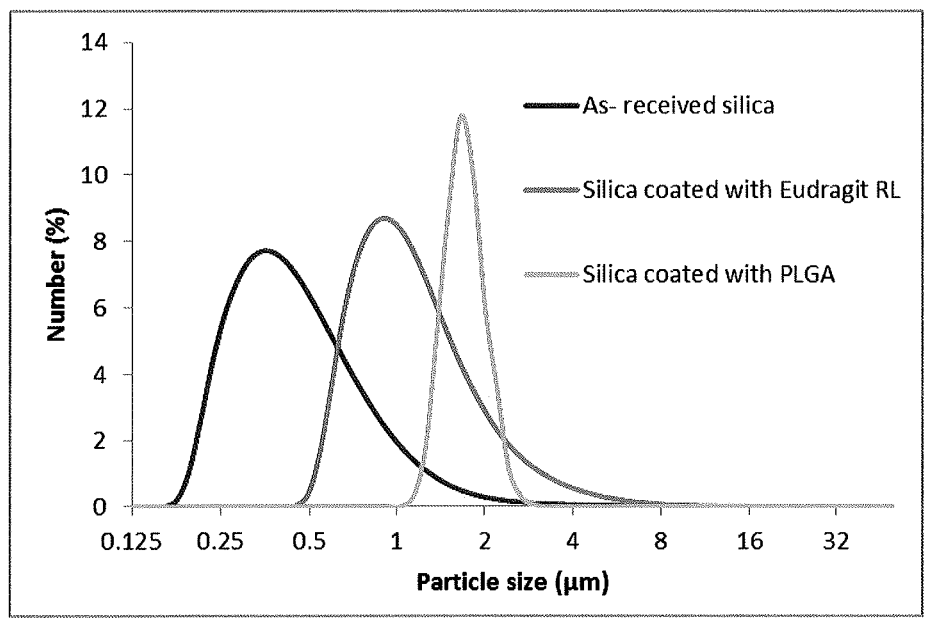
FIG. 17 is a plot of particle size distribution of as-received silica, Eudragit and PLGA coated silica.
Figure 18A:
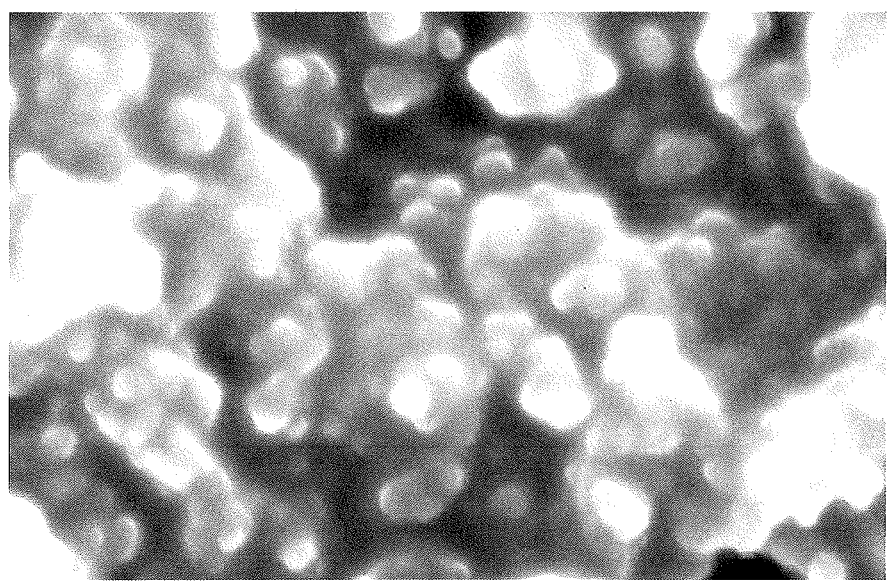
FIG. 18A is a SEM micrograph of polymer coated silica nanoparticles using the disclosed PHFAC process.
Figure 18B:
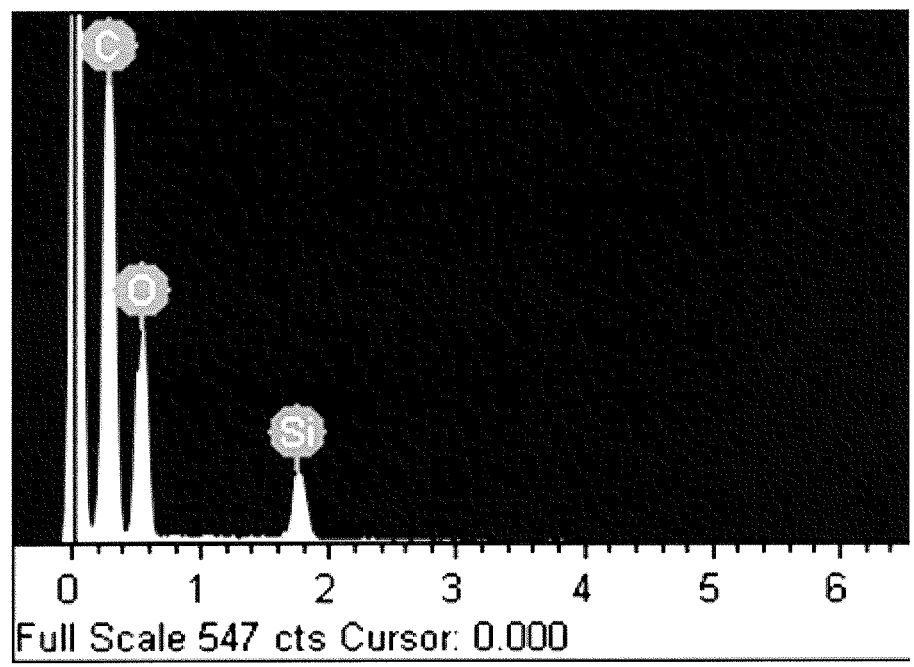
FIG. 18B are EDS results of polymer coated silica nanoparticles using the disclosed PHFAC process.
Figure 19:
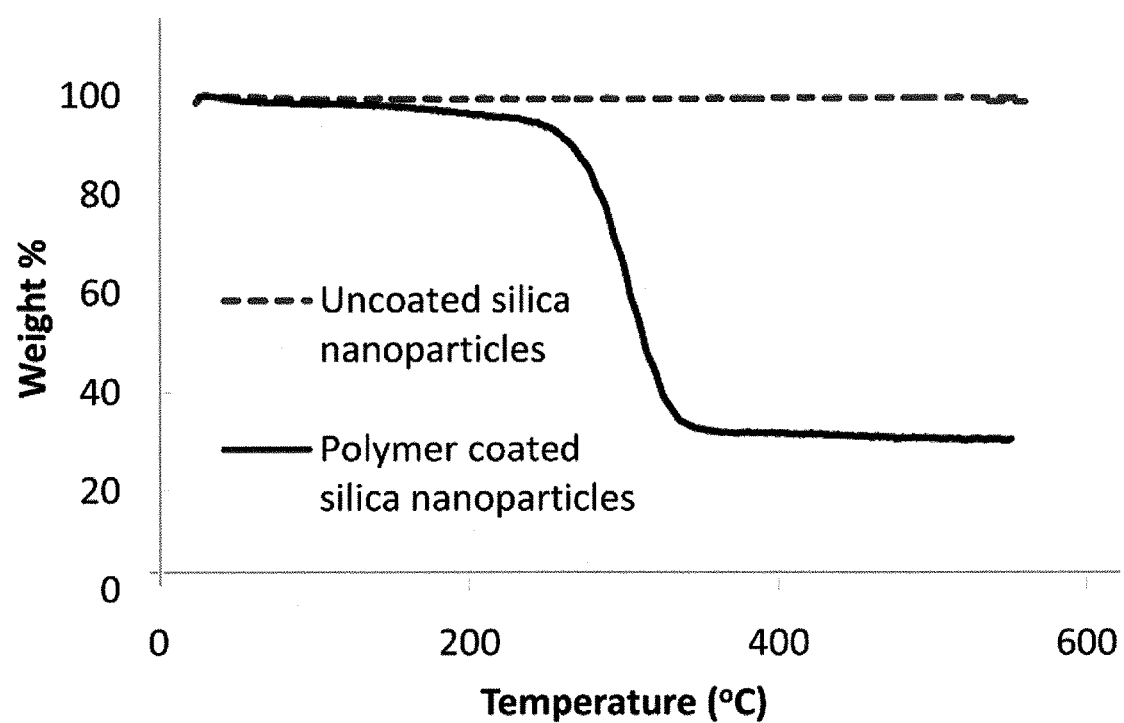
FIG. 19 provides TGA results of as-received silica nanoparticles as well as Eudragit RL coated silica nanoparticles.

The particle size distribution of the silica particles coated by Eudragit RL 100 or PLGA as well as the as-received silica particles was analyzed by laser diffraction to quantify the level of agglomeration of the particles after coating. FIG. 17 shows the results for the particle size distribution of the as-received silica, Eudragit-coated silica and PLGA-coated silica. The mean size of Eudragit coated silica was smaller than that of the PLGA coated silica as shown in Table 2 and FIG. 17. It is clear that the high level of particle connectivity witnessed in PLGA precipitation led to a greater agglomeration of coated particles.

TABLE 2

Specifications of PSD results for as-received silica, Eudragit coated silica and PLGA coated silica

|  | Mean size (µm) | $d_{10}$ (µm) | $d_{90}$ (µm) |
|---|---|---|---|
| As received silica | 0.595 | 0.266 | 0.969 |
| Eudragit coated silica | 1.398 | 0.704 | 2.324 |
| PLGA coated silica | 1.810 | 1.451 | 2.215 |

6. Comparisons of Two Different Polymer Coatings on Submicron-Size Silica Particles Both the tested polymers, Eudragit RL 100 and PLGA, were used to successfully coat the host silica particles. Each polymer has its own advantages as a coating material for the PHFAC process. Eudragit RL 100 produces somewhat more uniform coating and lesser amount of polymer bridging between neighboring silica particles; the coating thickness can be adjusted by controlling the amount of added silica in suspension for a given residence time. The coating formed by Eudragit is also thinner than that of PLGA. Agglomeration was also reduced considerably because of the smaller amount of polymer precipitation. On the other hand, PLGA is a widely used coating material especially in the field of drug delivery for controlled release. Due to the high sensitivity of the dioxane solutions of PLGA to the anti-solvent used, the coating thickness can also be adjusted simply by changing the concentration of PLGA in solution. From the results of FIG. 9 with Eudragit, one may expect that the amount of silica particles added to a solution can also influence the coating thickness.

7. Continuous Polymer Coating of Nanoparticles by PHFAC

Coating silica nanoparticles (Aerosil 200) by Eudragit RL 100 has also been studied using the disclosed PHFAC method, but not as extensively as the coating of the submicron silica particles. However, test results demonstrate that silica nanoparticles can be coated with the Eudragit RL 100 polymer as well. FIG. 18A provides a SEM micrograph of the coated silica nanoparticles. The micrograph shows that the silica particles were covered by the precipitated polymer, although there was a significant level of agglomeration among the coated particles. One reason for the agglomeration is that the silica particle size is so small (12 nm) that the particles have a strong tendency to stick to each other due to the strong van der Waals forces between the nanoparticles. Another reason is that the precipitated sticky polymer not only covers the particles but also connects the particles by forming polymer bridges between the particles. This type of agglomeration may be minimized by adding increased amounts of surfactants and applying sonication to break the soft bonding of the coated nanoparticles. FIG. 18B shows EDS results for the coated nanoparticles in which the carbon profile demonstrates that the nanoparticle was coated by the polymer since silica particles contain no carbon.

For the silica nanoparticles, TGA results are shown in FIG. 19. The blue curve represents the weight loss profile of the as-received silica nanoparticles as the temperature was increased to 550° C. There is negligible weight loss since silica nanoparticles do not decompose during the heating. However, the polymer-coated silica nanoparticles shown by the red curve have lost about 70% of the weight in the diagram since the polymer decomposed during the heating. The coating thickness on the nanoparticles can be estimated using equation (3) to be around 5 nm.

As demonstrated herein, an advantageous anti-solvent crystallization-based method using porous hollow fiber membranes has been developed for continuously synthesizing polymer-coated drug crystals in a PHFAC device. In devices and systems according to the present disclosure, the anti-solvent flowing through the lumen of porous hollow fibers is introduced through the pores in the wall of the fibers into the shell side where a solution (e.g., acetone-based solution) of a drug and a polymer (e.g., Eudragit) is flowing. The intense mixing created by the anti-solvent streaming jets into the feed solution generates very high supersaturation throughout the solution flowing in the shell side causing crystals (e.g., drug crystals) to appear very rapidly. Further, the crystals (e.g., GF crystals) are subsequently coated by a thin coating of the precipitating polymer leading to encapsulated crystals.

A variety of analytical techniques were used to characterize the coated drug and silica particles obtained according to exemplary implementations of the present disclosure. It was demonstrated that by applying the PHFAC method, one can get uniform and free-flowing coated drug/silica particles.

With specific reference to the drug testing described herein, results from XRD and Raman spectra and DSC measurements show that the polymer coating by the anti-solvent crystallization process did not alter the molecular structure of the drug. That the polymer-coated GF particles can be utilized for controlled release of the drug inside of the coating was demonstrated by drug dissolution testing since the percent drug dissolution was less than 20% after 50 minutes. Scale up of the process may be undertaken, e.g., by increasing the number of porous hollow fibers and the shell-side diameter, maintaining the shell-side residence time of the feed solution and the ratio of the feed flow rate to the anti-solvent flow rate to obtain coated drug particles having similar morphology and thickness of the polymer coating. Variations of the disclosed system/method may be implemented including introducing the drug and the polymer through the two different streams.

With specific reference to the silica-based implementations disclosed herein, the technique of porous hollow fiber anti-solvent crystallization (PHFAC) was successfully adapted to continuously coat submicron (550 nm) particles of silica with a polymer. After vacuum drying and sonication, free-flowing polymer-coated silica particles were obtained by this continuous process. By varying a number of conditions such as the silica loading in the solution-suspension and the solution concentration of the polymer, one can adjust the polymer coating thickness over certain ranges. Both the polymers, Eudragit RL 100 and PLGA, were used successfully to coat the silica particles using this novel method. Other experiments have shown that silica nanoparticles (12 nm) can also be successfully coated with a polymer by this process. This suggests that this continuous technique may be employed to encapsulate nanoparticles, submicron and micron-sized particles using different coating polymers.

Furthermore, by changing the material for the host particle and coating polymer, the disclosed PHFAC technique can be utilized in the production of cosmetics, personal care products, fertilizers, agricultural seeds, food and a range of pharmaceuticals.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

REFERENCES

[1] Langer, R. New Methods of Drug Delivery. Science, 1990, 249 (4976), 1527-1533.
[2] Lai, S. K.; Wang, Y. Y.; Hanes, J.; Mucus-penetrating nanoparticles for drug and gene delivery to mucosal tissues, Adv. Drug Deliv. Rev. 2008, 61 (2), 158-171.
[3] Nance, Elizabeth A.; Woodworth, Graeme F.; Sailor, Kurt A.; Shih, Ting-Yu.; Xu, Qingguo.; Swaminathan, Ganesh.; Xiang, Dennis.; Eberhart, Charles.; Hanes, Justin. A Dense Poly (Ethylene Glycol) Coating Improves Penetration of Large Polymeric Nanoparticles Within Brain Tissue. Science Translational Medicine 2012, 4 (149), 149-119.
[4] Oh, K. S.; Lee, K. E.; Han, S. S.; Cho, S. H.; Kim, D. Yuk, S. H. Formation of Core/Shell Nanoparticles with a Lipid Core and Their Application as a Drug Delivery System. Biomacromolecules, 2005, 6 (2), 1062-1067.
[5] Stejskal, J.; Trchová, M.; Brodinová, J.; Kalenda, P.; Fedorova, S. V.; Prokeš, J.; Zemek, J. Coating of zinc ferrite particles with a conducting polymer, polyaniline, Journal of Colloid and Interface Science, 2006, 298 (1), 87-93.
[6] Guiot, P.; Couvreur, P.; Eds. Polymeric Nanoparticles and Microspheres, Boca Raton, CRC Press, 1986.
[7] Korin, N.; Kanpathipillai, M. B.; Matthews, D.; Crescente, M.; Brill, A.; Mammoto, T.; Ghosh, K.; Jurek, S.; Bencherif, S. A.; Bhatta, D.; Coskun, A. U.; Feldman, C. L.; Wagner, D. D.; Ingber, D. E. Shear-Activated Nanotherapeutics for Drug Targeting to Obstructed Blood Vessels. Science, 2012, 337, 738-742.
[8] Leong, K. W.; Mao, H.-Q.; Truong-Le, V. L.; Roy, K.; Walsh, S. M.; August, J. T. DNA-polycation Nanospheres as Non-viral Gene Delivery Vehicles. J. Control. Rel. 1998, 53 (1-3), 183-193.
[9] Gelperina, S.; Kisich, K.; Iseman, M. D.; Heifets, L. The Potential Advantages of Nanoparticle Drug Delivery Systems in Chemotherapy of Tuberculosis. American Journal of Respiratory and Critical Care Medicine. 2005, 172, 1487.
[10] Yue, B.; Yang, J.; Wang, Y.; Huang, M.; Dave, R.; Pfeffer, R. Particle Encapsulation with Polymers via in-situ Polymerization in Supercritical $CO_2$. Powder Technol. 2004, 146 (1-2), 32.
[11] Wang, Y.; Dave, R. N.; Pfeffer, R. Polymer Coating/encapsulation of Nanoparticles using a Supercritical Antisolvent Process. J. Supercritical Fluids. 2004, 28, 84.
[12] Kim, J. H.; Paxton, T. E.; Tomasko, D. L. Microencapsulation of Naproxen using Rapid Expansion of Supercritical Solutions. Biotechnol. Prog. 1996, 12, 650-661.
[13] Pessey, V.; Mateos, D.; Weill, F.; Cansell, F.; Etourneau, J.; Chevalier, B. $SmCO_5$/CU Particles Elaboration using a Supercritical Fluid Process. J. Alloys Compounds 2001, 323, 412-416.
[14] Falk, R.; Randolph, T. W.; Meyer, J. D.; Kelly, R. M.; Manning, M. C. Controlled Release of Ionic Compounds from Poly (L-lactide) Microspheres Produced by Precipitation with a Compressed Antisolvent. J. Control. Release 1997, 44, 77-85.
[15] Tsutsumi, A.; Nakamoto, S.; Mineo, T.; Yoshida, K. A Novel Fuidized-bed Coating of Fine Particles by Rapid Expansion of Supercritical Fluid Solutions. Powder Technol. 1995, 85, 275.
[16] Myerson, A. S. Handbook of Industrial Crystallization. 2nd Ed. Butterworth-Heinemann, Boston, Mass. (2002).
[17] Tavare, N. S; Micromixing Limits in an MSMPR Crystallizer Chemical Engineering Technology 1989, 12, 1-12.
[18] Midler, M.; Paul, E. L.; Whittington, E. F.; Futran, M.; Liu, P. D.; Hsu, J.; Pan, S. H. 1994. Crystallization Method to Improve Crystal Structure and Size. U.S. Pat. No. 5,314,506.
[19] Zarkadas, D. M.; K. K. Sirkar, Antisolvent Crystallization in Porous Hollow Fiber Devices, Chem. Eng. Sci., 2006, 61, 5030-5048.
[20] Chen, D. C.; Singh, D.; Sirkar, K. K.; Pfeffer, R. Continuous Polymer Coating/encapsulation of Submicron Particles using a Solid Hollow Fiber Cooling Crystallization Method, I&E Chem. Res., 2014, 53, 6388-6400.
[21] Chen, D. C.; Singh, D.; Sirkar, K. K.; Zhu, J.; Pfeffer, R. Continuous Polymer Nanocoating on Silica Nanoparticles, Langmuir, 2014, 30, 7804-7810.

The invention claimed is:
1. A method for coating a material, comprising:
a) providing a polymer solution containing a polymer and a material to be coated by the polymer;
b) passing the polymer solution around an exterior of a hollow fiber; and
c) passing an anti-solvent through a lumen of the hollow fiber so that the anti-solvent permeates through pores of the hollow fiber and travels to the exterior of the hollow fiber and exposes the anti-solvent to the polymer solution, thereby causing the polymer to precipitate on the material, with precipitated polymer forming a coating on the material.
2. The method of claim 1, wherein the material is suspended in the polymer solution.

3. The method of claim 1, wherein the material is in solution in the polymer solution, and wherein the material precipitates from the polymer solution in response to exposure to the anti-solvent.

4. The method of claim 1, wherein the material is a drug.

5. The method of claim 1, wherein the hollow fiber has an internal diameter of about 600 µm and an outer diameter of about 1000 µm.

6. The method of claim 1, wherein the hollow fiber has a fiber wall porosity of about 0.75.

7. The method of claim 1, wherein the pores of the hollow fiber have pores sizes from about 0.2 µm to about 1.5 µm.

8. The method of claim 1, wherein the material is suspended in the polymer solution as submicron or nano-sized particles.

9. The method of claim 1, wherein the hollow fiber is hydrophilic and is fabricated from nylon.

10. The method of claim 1, wherein the anti-solvent is passed through the lumen at a first pressure level and the polymer solution is passed around the exterior of the hollow fiber at a second pressure level, the first pressure level higher than the second pressure level.

11. The method of claim 1, wherein the polymer solution includes a copolymer of methyl methacrylate, ethyl acrylate and methacrylic acid ester.

12. The method of claim 1, wherein the polymer solution includes Poly (D, L-lactide-co-glycolide.

13. The method of claim 1, wherein the material is suspended in the polymer solution and the material includes Griseofulvin drug particles.

14. The method of claim 1, wherein the coating thickness of the polymer on the particles is from about 5 nm to about 75 nm.

15. A method for coating particles comprising:
a) providing a polymer solution containing a polymer and a suspension of particles;
b) passing the polymer solution around an exterior of a plurality of hollow fibers; and
c) passing an anti-solvent through respective lumina of the plurality of hollow fibers so that the anti-solvent permeates through pores of each respective hollow fiber and travels to the exterior of the hollow fibers and exposes the anti-solvent to the polymer solution, thereby causing the polymer to precipitate on the particles, with precipitated polymer forming a coating on the particles.

16. The method of claim 15, wherein each hollow fiber of the plurality of hollow fibers is disposed within a tubing.

17. The method of claim 15, wherein the anti-solvent is passed through the lumina at a first pressure level and the polymer solution is passed around the exterior of the hollow fibers at a second pressure level, the first pressure level higher than the second pressure level.

18. A method for coating particles comprising:
a) providing a solution containing a polymer and drug;
b) passing the solution through a lumen of a hollow fiber or around an exterior to the hollow fiber; and
c) passing an anti-solvent around the exterior of the hollow fiber in an instance where the solution is passed through the lumen of the hollow fiber, or through the lumen of the hollow fiber in an instance where the solution is passed around the exterior to the hollow fiber, so that the anti-solvent or the solution permeates through pores of the hollow fiber and travels to the lumen of the hollow fiber and exposes the anti-solvent to the solution, thereby causing the polymer to precipitate on the drug, with precipitated polymer forming a coating on the particles of the drug.

19. The method of claim 18, wherein the solution is a polymer solution, and wherein the drug is suspended in the polymer solution.

* * * * *